US011407787B2

(12) United States Patent
Fujimoto et al.

(10) Patent No.: US 11,407,787 B2
(45) Date of Patent: Aug. 9, 2022

(54) CRYSTAL OF OXIDIZED GLUTATHIONE DICATION SALT AND PRODUCTION METHOD THEREFOR

(71) Applicant: KYOWA HAKKO BIO CO., LTD., Tokyo (JP)

(72) Inventors: Akihiro Fujimoto, Tokyo (JP); Kazunari Fukumoto, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 16/619,081

(22) PCT Filed: Jun. 6, 2018

(86) PCT No.: PCT/JP2018/021712
§ 371 (c)(1),
(2) Date: Dec. 3, 2019

(87) PCT Pub. No.: WO2018/225790
PCT Pub. Date: Dec. 13, 2018

(65) Prior Publication Data
US 2020/0095279 A1    Mar. 26, 2020

(30) Foreign Application Priority Data

Jun. 8, 2017 (JP) .............................. JP2017-113315

(51) Int. Cl.
*C07K 5/093* (2006.01)

(52) U.S. Cl.
CPC ........ *C07K 5/0819* (2013.01); *C07B 2200/13* (2013.01)

(58) Field of Classification Search
None
See application file for complete search history.

(56) References Cited

U.S. PATENT DOCUMENTS

| 9,000,126 | B2 * | 4/2015 | Kimura | .................. | C30B 29/54 |
| | | | | | 530/331 |
| 2004/0250751 | A1 * | 12/2004 | Shimose | ................ | A61P 39/02 |
| | | | | | 117/84 |
| 2013/0035470 | A1 * | 2/2013 | Kimura | .................. | C30B 29/54 |
| | | | | | 530/331 |
| 2014/0194371 | A1 * | 7/2014 | Mouri | ...................... | A23L 2/52 |
| | | | | | 514/21.8 |
| 2015/0175653 | A1 | 6/2015 | Kimura et al. | | |
| 2018/0094025 | A1 | 4/2018 | Ooshima et al. | | |
| 2018/0305388 | A1 | 10/2018 | Abe et al. | | |

FOREIGN PATENT DOCUMENTS

| CN | 101955511 | * | 1/2011 |
| CN | 101955511 A | | 1/2011 |
| EP | 2727932 A1 | | 5/2014 |
| JP | 6055408 B2 | * | 12/2016 |
| WO | WO 2003/035674 A1 | | 5/2003 |
| WO | WO 2011/132724 A1 | | 10/2011 |
| WO | WO 2013/002317 | * | 1/2013 |
| WO | WO 2013/002317 A1 | | 1/2013 |
| WO | WO 2016/159317 A1 | | 10/2016 |
| WO | WO 2017/086443 A1 | | 5/2017 |

OTHER PUBLICATIONS

Diaion (downloaded on Apr. 10, 2021 from URL:< http://www.itochu-ca.com/docs/product/00500-013.pdf >) (Year: 2021).*
Jelsch et al., "The oxidized form of glutathione," *Acta Cryst.*, C55: 1538-1540 (1999).
Japanese Patent Office, International Preliminary Report on Patentability in International Patent Application No. PCT/JP2018/021712 (dated Dec. 10, 2019).
Japanese Patent Office, International Search Report in International Patent Application No. PCT/JP2018/021712 (dated Sep. 4, 2018).
Miyoshi et al., "Crystal Structure and Spectroscopic Properties of Violet Glutathione-Copper(II) Complex with Axial Sulfur Coordination and Two Copper Sites vis a Disulfide Bridge," *J. Am. Chem. Soc.*, 102(19): 6130-6136 (1980).
European Patent Office, Extended European Search Report in European Patent Application No. 18813907.5 (dated Feb. 11, 2021).
Hiiro, "(Lecture 14) Ion Exchange," *Journal of Environmental Conservation Engineering*, 9(8): 637-643 (1980).

* cited by examiner

*Primary Examiner* — Sergio Coffa
(74) *Attorney, Agent, or Firm* — Leydig, Voit & Mayer, Ltd.

(57) ABSTRACT

The present application discloses a crystal of oxidized glutathione dication salt and a method of producing the same.

9 Claims, 8 Drawing Sheets

CRYSTAL OF OXIDIZED GLUTATHIONE DICATION SALT AND PRODUCTION METHOD THEREFOR

CROSS-REFERENCE TO RELATED APPLICATIONS

This patent application is the U.S. national phase of International Patent Application No. PCT/JP2018/021712, filed Jun. 6, 2018, which claims the benefit of Japanese Patent Application No. 2017-113315, filed Jun. 8, 2017, which are incorporated by reference in their entireties herein.

TECHNICAL FIELD

The present invention relates to a crystal of oxidized glutathione (hereinafter referred to as GSSG) dication salt useful, for example, as products, raw materials or intermediates of health foods, pharmaceuticals or cosmetics, and a method of producing the same.

BACKGROUND ART

GSSG has a structure in which two molecules of reduced glutathione (hereinafter referred to as GSH) are bonded through a disulfide bond, the structure having two carboxyl groups in the molecule.

As a crystal of free GSSG, a crystal of octahydrate (Non Patent Document 1), a crystal of monohydrate (Patent Document 1) and a crystal of hexahydrate (Patent Document 2) have been known so far. However, since any of these crystals has low solubility in water, an aqueous solution of GSSG with a high concentration cannot be prepared.

Although a crystal of cation-containing monoammonium salt has been acquired as a crystal of GSSG with improved solubility in comparison with free GSSG, the solubility thereof in water at 25° C. is 34.8 mass %, i.e., regarded as insufficient (Table 1 in Patent Document 3). Diammonium salt which similarly contains a cation has not been acquired even a non-crystalline amorphous in solid, and there is no knowledge on the crystal thereof (Patent Document 3). Furthermore, there is no knowledge on crystals of disodium salt and dilithium salt so far, and due to the nature of the compound, the very high deliquescence is regarded as unsuitable for industrial use (Patent Document 3).

RELATED ART

Patent Document

Patent Document 1: International Publication No. WO 2003/035674
Patent Document 2: International Publication No. WO 2011/132724
Patent Document 3: International Publication No. WO 2013/002317

Non Patent Document

Non Patent Document 1: Jelsch et al., "The oxidized form of glutathione", Acta Crystallographica Section C: Crystal Structure Communications, International Union of Crystallography, p 1538-1540, 1999

DISCLOSURE OF INVENTION

Problems to Be Solved by the Invention

An object of the present invention is to provide a crystal of oxidized glutathione dication salt excellent in solubility and storage stability, and a method of producing the same.

Means for Solving the Problems

The present invention relates to the following (1) to (28):
(1) A crystal of oxidized glutathione (hereinafter referred to as GSSG) dication salt.
(2) The crystal according to (1) above, the crystal being a crystal of GSSG disodium salt hexahydrate.
(3) The crystal according to (2) above, the crystal having peaks at diffraction angles $2\theta(°)$ of $18.5±0.2°$, $20.7±0.2°$, $21.3±0.2°$, $23.2±0.2°$ and $23.6±0.2°$ in powder X-ray diffraction.
(4) The crystal according to (3) above, the crystal having peaks at diffraction angles $2\theta(°)$ of $18.9±0.2°$, $6.4±0.2°$, $22.5±0.2°$, $12.7±0.2°$ and $19.4±0.2°$ in powder X-ray diffraction.
(5) The crystal according to (4) above, the crystal having peaks at diffraction angles $2\theta(°)$ of $22.0±0.2°$, $19.9±0.2°$, $22.8±0.2°$, $25.6±0.2°$ and $24.4±0.2°$ in powder X-ray diffraction.
(6) The crystal according to (1) above, the crystal being a crystal of GSSG dipotassium salt trihydrate.
(7) The crystal according to (6) above, the crystal having peaks at diffraction angles $2\theta(°)$ of $23.8±0.2°$, $22.1±0.2°$, $21.6±0.2°$, $25.0±0.2°$ and $20.4±0.2°$ in powder X-ray diffraction.
(8) The crystal according to (7) above, the crystal having peaks at diffraction angles $2\theta(°)$ of $17.5±0.2°$, $25.6±0.2°$, $26.7±0.2°$, $23.3±0.2°$ and $18.1±0.2°$ in powder X-ray diffraction.
(9) The crystal according to (8) above, the crystal having peaks at diffraction angles $2\theta(°)$ of $28.5±0.2°$, $27.8±0.2°$, $19.2±0.2°$, $19.7±0.2°$ and $31.5±0.2°$ in powder X-ray diffraction.
(10) The crystal according to (1) above, the crystal being a crystal of GSSG dilithium salt trihydrate.
(11) The crystal according to (10) above, the crystal having peaks at diffraction angles $2\theta(°)$ of $18.9±0.2°$, $19.3±0.2°$, $20.1±0.2°$, $20.5±0.2°$ and $23.5±0.2°$ in powder X-ray diffraction.
(12) The crystal according to (11) above, the crystal having peaks at diffraction angles $2\theta(°)$ of $24.6±0.2°$, $21.3±0.2°$, $20.3±0.2°$, $25.9±0.2°$ and $20.9±0.2°$ in powder X-ray diffraction.
(13) The crystal according to (12) above, the crystal having peaks at diffraction angles $2\theta(°)$ of $24.0±0.2°$, $4.6±0.2°$, $26.2±0.2°$, $26.5±0.2°$ and $22.2±0.2°$ in powder X-ray diffraction.
(14) The crystal according to (1) above, the crystal being a crystal of GSSG diammonium salt trihydrate.
(15) The crystal according to (14) above, the crystal having peaks at diffraction angles $2\theta(°)$ of $15.8±0.2°$, $24.6±0.2°$, $24.3±0.2°$, $10.5±0.2°$ and $20.9±0.2°$ in powder X-ray diffraction.
(16) The crystal according to (15) above, the crystal having peaks at diffraction angles $2\theta(°)$ of $18.5±0.2°$, $14.7±0.2°$, $22.2±0.2°$, $5.7±0.2°$ and $16.7±0.2°$ in powder X-ray diffraction.

(17) The crystal according to (16) above, the crystal having peaks at diffraction angles 2θ(°) of 19.5±0.2°, 17.1±0.2°, 15.2±0.2°, 23.8±0.2° and 8.3±0.2° in powder X-ray diffraction.

(18) A method of producing a crystal of GSSG dication salt comprising a step of leaving a non-crystalline amorphous GSSG dication salt to stand for 48 hours or more.

(19) A method of producing a crystal of GSSG dication salt comprising a step of dropping or adding alcohol to an aqueous solution of GSSG dissolving a cation-containing compound, a step of adding a crystal of GSSG dication salt as a seed crystal to the aqueous solution to precipitate the crystal of GSSG dication salt, and a step of collecting the crystal of GSSG dication salt from the aqueous solution.

(20) The method according to (19) above, wherein the alcohol to be dropped or added is selected from the group consisting of C1 to C6 alcohols.

(21) The method according to (18) above, wherein the non-crystalline amorphous GSSG dication salt is a non-crystalline amorphous GSSG disodium salt, and the crystal of GSSG dication salt is a crystal of GSSG disodium salt hexahydrate.

(22) The method according to (18) above, wherein the non-crystalline amorphous GSSG dication salt is a non-crystalline amorphous GSSG dipotassium salt, and the crystal of GSSG dication salt is a crystal of GSSG dipotassium salt trihydrate.

(23) The method according to (18) above, wherein the non-crystalline amorphous GSSG dication salt is a non-crystalline amorphous GSSG dilithium salt, and the crystal of GSSG dication salt is a crystal of GSSG dilithium salt trihydrate.

(24) The method according to (18) above, wherein the non-crystalline amorphous GSSG dication salt is a non-crystalline amorphous GSSG diammonium salt, and the crystal of GSSG dication salt is a crystal of GSSG diammonium salt trihydrate.

(25) The method according to (19) or (20) above, wherein the cation-containing compound is a sodium-containing compound, and the crystal of GSSG dication salt is a crystal of GSSG disodium salt hexahydrate.

(26) The method according to (19) or (20) above, wherein the cation-containing compound is a potassium-containing compound, and the crystal of GSSG dication salt is a crystal of GSSG dipotassium salt trihydrate.

(27) The method according to (19) or (20) above, wherein the cation-containing compound is a lithium-containing compound, and the crystal of GSSG dication salt is a crystal of GSSG dilithium salt trihydrate.

(28) The method according to (19) or (20) above, wherein the cation-containing compound is an ammonium-containing compound, and the crystal of GSSG dication salt is a crystal of GSSG diammonium salt trihydrate.

Effects of the Invention

According to the present invention, a crystal of GSSG dication salt excellent in solubility and storage stability, and a method of producing the same are provided.

EMBODIMENTS FOR CARRYING OUT THE INVENTION

1. Crystal of the Present Invention

Figure 1:
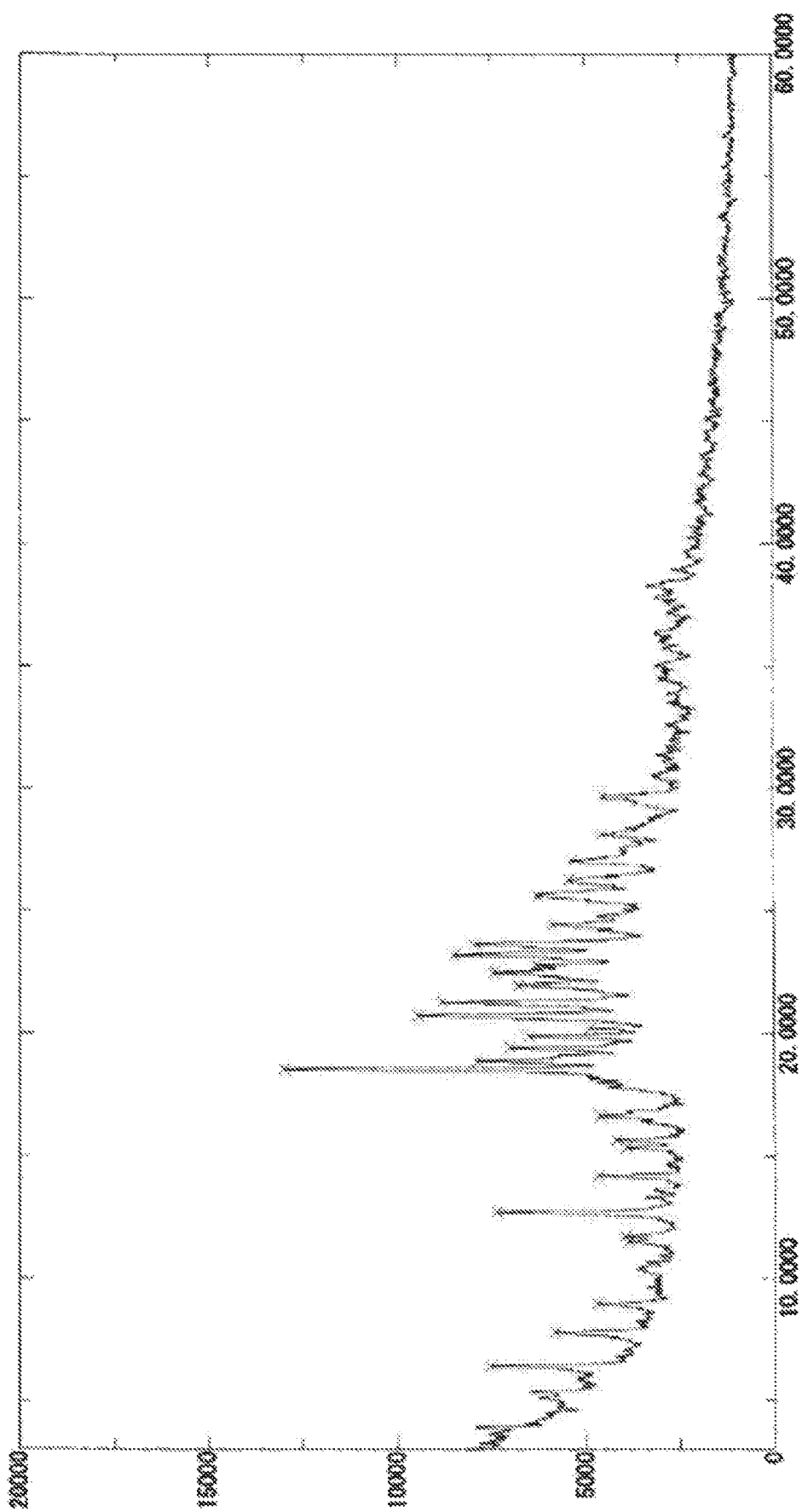
FIG. 1 illustrates the results of powder X-ray diffraction of a crystal of GSSG disodium salt hexahydrate obtained in Example 1. The vertical axis represents intensity (cps), and the horizontal axis represents a diffraction angle 2θ(°).

The crystal of the present invention is a crystal of GSSG dication salt.

The crystal of the present invention may be a crystal of salt containing GSSG ions and cations at a ratio of 1:2 without particular limitation on the type of cation, and for example, thereof include a crystal of salt containing GSSG ions and sodium ions at a ratio of 1:2 (hereinafter referred to as the crystal of GSSG disodium salt), a crystal of salt containing GSSG ions and potassium ions at a ratio of 1:2 (hereinafter referred to as the crystal of GSSG dipotassium salt), a crystal of salt containing GSSG ions and lithium ions at a ratio of 1:2 (hereinafter referred to as the crystal of GSSG dilithium salt), and a crystal of salt containing GSSG ions and ammonium ions at a ratio of 1:2 (hereinafter referred to as the crystal of GSSG diammonium salt).

1-1. Crystal of GSSG Disodium Salt

It can be confirmed that the crystal of GSSG disodium salt is a crystal of GSSG by, for example, analysis using high performance liquid chromatograph (HPLC).

Examples of the analysis conditions in the analysis using HPLC include the following conditions:
Column: Inertsil ODS-3 (150 mm×3 mm ID)
Column temperature: 35° C.
Mobile phase: In 1000 mL of water, 6.8 g of potassium dihydrogen phosphate and 2.0 g of sodium 1-heptanesulfonate are dissolved, and then phosphoric acid is added thereto to adjust the pH to 3.0. To 970 mL of the solution, 30 mL of methanol is added for use as mobile phase.
Flow rate: 0.5 mL/min
Detector: UV detector (wavelength: 210 nm)

It can be confirmed that the crystal is crystal of a GSSG disodium salt also by analysis by powder X-ray diffraction.

The analysis by powder X-ray diffraction can be performed, for example, by using a powder X-ray diffractometer (XRD) Ultima IV (manufactured by Rigaku Corporation) with CuKα as the X-ray source, according to the attached instruction manual.

Although the crystal of GSSG disodium salt may be a crystal of anhydrate or a crystal of hydrate, preferred examples include a crystal of hydrate, more preferred a crystal of hexahydrate.

Specific examples of the crystal of such a hexahydrate include a crystal of GSSG disodium salt hexahydrate represented by composition formula $[C_{20}H_{30}N_6O_{12}S_2Na_2]\cdot 6H_2O$.

It can be confirmed that the crystal of GSSG disodium salt is a crystal of sodium salt, through measurement of the sodium content in the crystal by atomic absorption analysis or high-frequency inductively coupled plasma (ICP) emission spectroscopy.

Atomic absorption analysis can be performed, for example, using an atomic absorption photometer Z-2310 (manufactured by Hitachi High-Technologies Corporation) in accordance with the attached instruction manual. ICP emission spectroscopy can be performed, for example, using an ICP emission spectrophotometer ICPS-8100 (manufactured by Shimadzu Corporation) in accordance with the attached instruction manual.

Although the sodium content in a crystal of GSSG disodium salt varies depending on the number of hydrated water contained in the crystal, it can be confirmed that when the crystal of GSSG disodium salt is a crystal of hexahydrate, the crystal of GSSG disodium salt is a crystal of disodium salt, by a sodium content in the crystal of usually 7.0±1.0 wt %, preferably 7.0±0.7 wt %, and most preferably 7.0±0.5 wt %, in terms of anhydrite.

It can be confirmed that the crystal of GSSG disodium salt is a crystal of hexahydrate, by a water content in the crystal of usually 14.1±2.0 wt %, preferably 14.1±1.5 wt %, and more preferably 14.1±1.0%.

The water content can be measured, for example, by the Karl-Fischer method or thermogravimetry differential thermal analysis.

The water content measurement by the Karl-Fischer method may be performed by using, for example, MKA-510N/MKS-510N (manufactured by Kyoto Electronics Manufacturing Co., Ltd.) in accordance with the attached instruction manual.

Examples of the crystal of GSSG disodium salt include a crystal having peaks at diffraction angles 2θ(°) described in the following (i) in powder X-ray diffraction with CuKα as the X-ray source. A crystal having peaks at diffraction angles 2θ(°) described in the following (i) and (ii) is preferred, and a crystal having peaks at diffraction angles 2θ (°) described in the following (i), (ii) and (iii) is more preferred.

(i) 18.5±0.2°, preferably ±0.1°; 20.7±0.2°, preferably ±0.1°; 21.3±0.2°, preferably ±0.1°; 23.2±0.2°, preferably ±0.1°; and 23.6±0.2°, preferably ±0.1°.

(ii) 18.9±0.2°, preferably ±0.1°; 6.4±0.2°, preferably ±0.1°; 22.5±0.2°, preferably ±0.1°; 12.7±0.2°, preferably ±0.1°; and 19.4±0.2°, preferably ±0.1°.

(iii) 22.0±0.2°, preferably ±0.1°; 19.9±0.2°, preferably ±0.1°; 22.8±0.2°, preferably ±0.1°; 25.6±0.2°, preferably ±0.1° and 24.4±0.2°, preferably ±0.1°.

Figure 2:
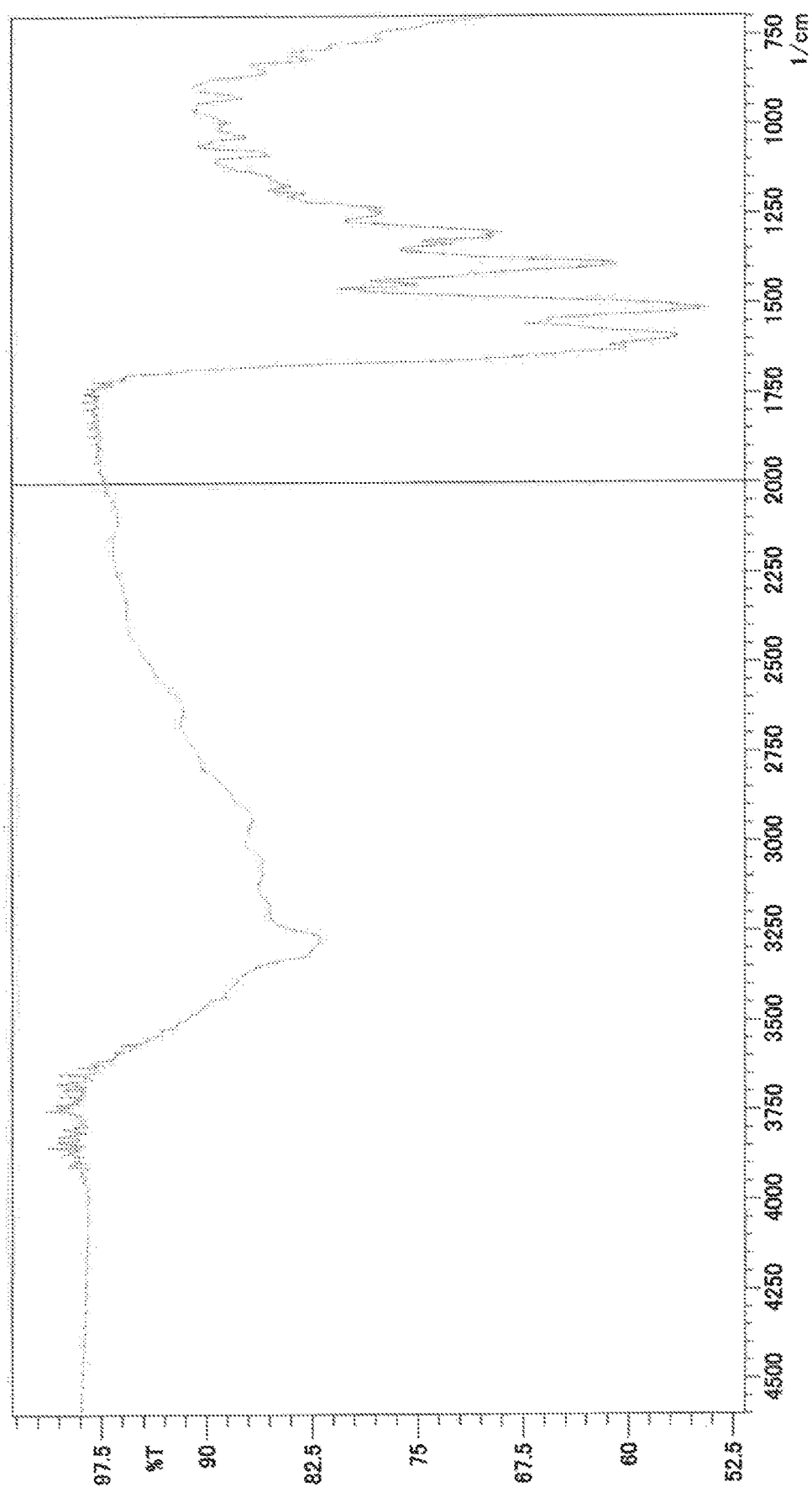
FIG. 2 illustrates the results of infrared spectroscopic (IR) analysis of a crystal of GSSG disodium salt hexahydrate obtained in Example 1. The vertical axis represents transmittance of light (% T), and the horizontal axis represents wavenumber (cm$^{-1}$).

Specific examples of the crystal of GSSG disodium salt include a crystal of GSSG disodium salt hexahydrate of which powder X-ray diffraction pattern with use of CuKα as X-ray source is specified by the pattern shown in FIG. 1 and the diffraction angle values described in Table 1, and a crystal of GSSG disodium salt hexahydrate having an infrared absorption spectrum shown in FIG. 2 in infrared spectroscopic (IR) analysis.

The infrared spectroscopic (IR) analysis may be performed, for example, using FTIR-8400 type (manufactured by Shimadzu Corporation) in accordance with the attached instruction manual.

1-2. Crystal of GSSG Dipotassium Salt

It can be confirmed that the crystal of GSSG dipotassium salt is a crystal of GSSG by, for example, the same analysis using HPLC as in 1-1 described above.

It can be also confirmed that the crystal is a crystal of GSSG dipotassium salt, by the same powder X-ray diffraction analysis as in 1-1 described above.

Although the crystal of GSSG dipotassium salt may be a crystal of anhydrate or a crystal of hydrate, preferred examples include a crystal of hydrate and more preferred examples include a crystal of trihydrate.

Specific examples of the crystal of such a trihydrate include a crystal of GSSG dipotassium salt trihydrate represented by composition formula $[C_{20}H_{30}N_6O_{12}S_2K_2]\cdot 3H_2O$.

It can be confirmed that the crystal of GSSG dipotassium salt is a crystal of potassium salt, through measurement of the potassium content in the crystal by atomic absorption analysis or ICP emission spectroscopy.

Although the potassium content in the crystal of GSSG dipotassium salt varies depending on the number of hydrated water contained in the crystal, it can be confirmed that when the crystal of GSSG dipotassium salt is a crystal of trihydrate, the crystal of GSSG dipotassium salt is a crystal of dipotassium salt, by a potassium content in the crystal of usually 11.4±2.0 wt %, preferably 11.4±1.6 wt %, and most preferably 11.4±1.2 wt % in terms of anhydrate.

It can be confirmed that the crystal of GSSG dipotassium salt is a crystal of trihydrate, by a water content in the crystal of usually 7.3±1.0 wt %, preferably 7.3±0.7 wt %, and more preferably 7.3±0.5 wt % as determined by the Karl-Fischer method or thermogravimetry differential thermal analysis.

The measurement of water content by the Karl-Fischer method may be performed in the same manner as in 1-1 described above.

Examples of the crystal of GSSG dipotassium salt include a crystal having peaks at diffraction angles 2θ(°) described in the following (iv) in powder X-ray diffraction with CuKα as the X-ray source. A crystal having peaks at diffraction angles 2θ(°) described in the following (iv) and (v) is preferred, and a crystal having peaks at diffraction angles 2θ(°) described in the following (iv), (v) and (vi) is more preferred.

(iv) 23.8±0.2°, preferably ±0.1°; 22.1±0.2°, preferably ±0.1°; 21.6±0.2°, preferably ±0.1°; 25.0±0.2°, preferably ±0.1°; and 20.4±0.2°, preferably ±0.1°.

(v) 17.5±0.2°, preferably ±0.1°; 25.6±0.2°, preferably ±0.1°; 26.7±0.2°, preferably ±0.1°; 23.3±0.2°, preferably ±0.1°; and 18.1±0.2°, preferably ±0.1°.

(vi) 28.5±0.2°, preferably ±0.1°; 27.8±0.2°, preferably ±0.1°; 19.2±0.2°, preferably ±0.1°; 19.7±0.2°, preferably ±0.1° and 31.5±0.2°, preferably ±0.1°.

Figure 3:
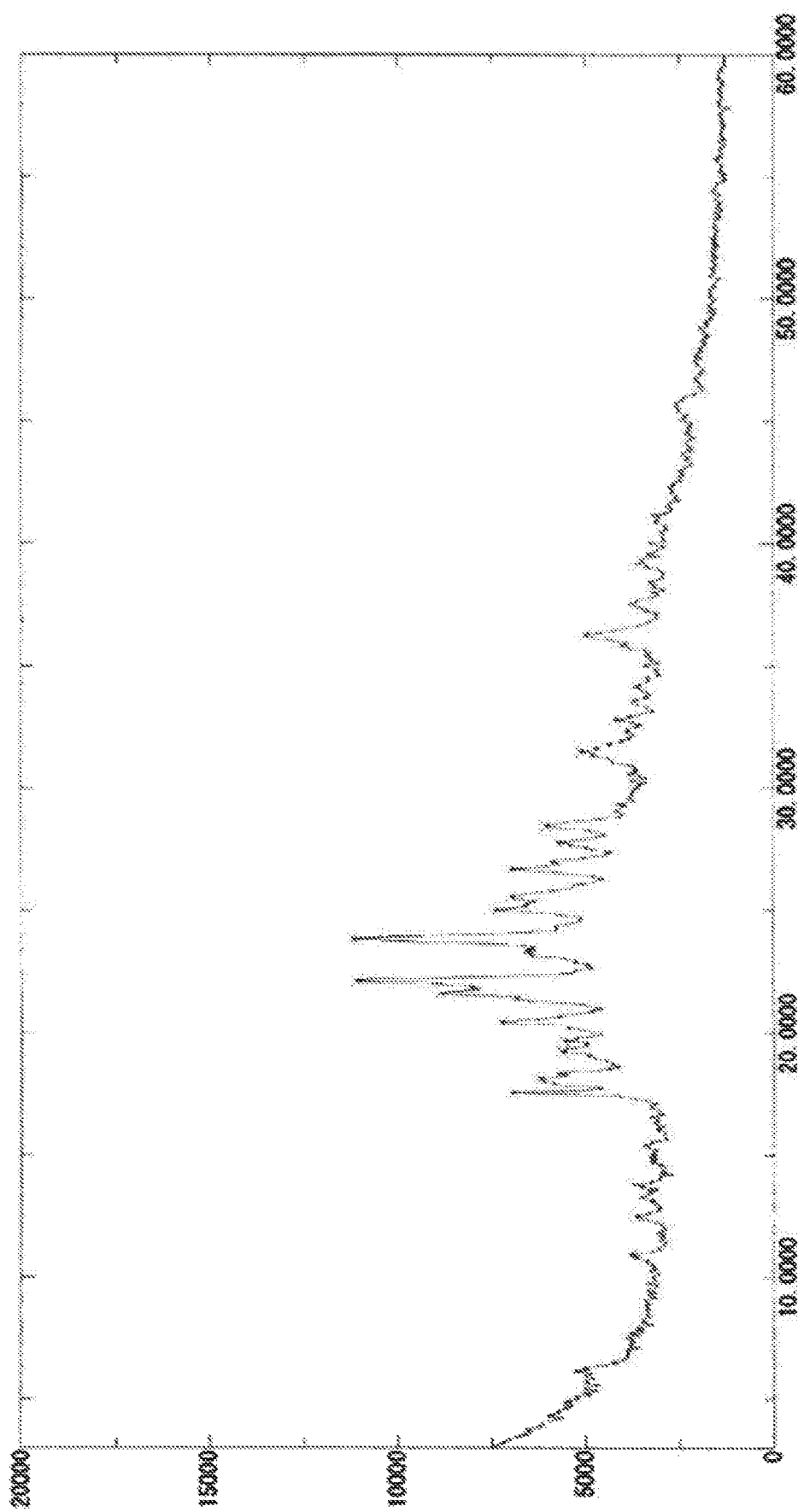
FIG. 3 illustrates the results of powder X-ray diffraction of a crystal of GSSG dipotassium salt trihydrate obtained in Example 2. The vertical axis represents intensity (cps), and the horizontal axis represents diffraction angle 2θ(°).
Figure 4:
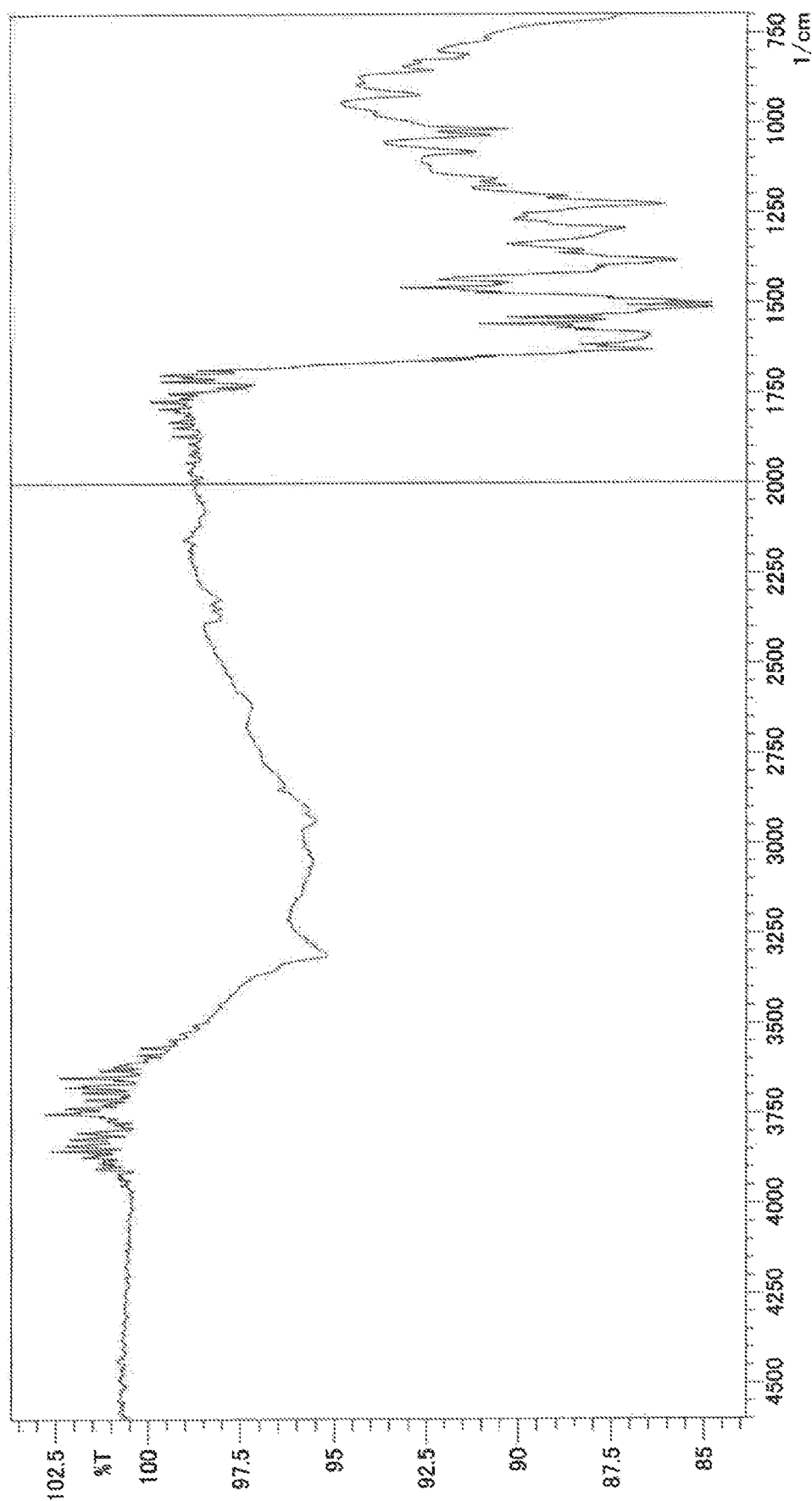
FIG. 4 illustrates the results of infrared spectroscopic (IR) analysis of a crystal of GSSG dipotassium salt trihydrate obtained in Example 2. The vertical axis represents the transmittance of light (% T), and the horizontal axis represents wavenumber (cm$^{-1}$).

Specific examples of the crystal of GSSG dipotassium salt include a crystal of GSSG dipotassium salt trihydrate of which powder X-ray diffraction pattern with use of CuKα as the X-ray source is specified by the pattern shown in FIG. 3 and the diffraction angle values described in Table 2, or a crystal of GSSG dipotassium salt trihydrate having an infrared absorption spectrum shown in FIG. 4 in infrared spectroscopic (IR) analysis.

The infrared spectroscopic (IR) analysis may be performed in the same manner as in 1-1 described above.

1-3. Crystal of GSSG Dilithium Salt

It can be confirmed that the crystal of GSSG dilithium salt is a crystal of GSSG by, for example, the same analysis using HPLC as in 1-1 described above.

It can be also confirmed that the crystal is a crystal of GSSG dilithium salt, by the same powder X-ray diffraction analysis as in 1-1 described above.

Although the crystal of GSSG dilithium salt may be a crystal of anhydrate or a crystal of hydrate, preferred examples include a crystal of hydrate, and more preferred a crystal of trihydrate.

Specific examples of the crystal of such trihydrate include a crystal of GSSG dilithium salt trihydrate represented by composition formula $[C_{20}H_{30}N_6O_{12}S_2Li_2]3H_2O$.

It can be confirmed that the crystal of GSSG dilithium salt is a crystal of lithium salt, through measurement of the lithium content in the crystal by atomic absorption analysis or ICP emission spectroscopy.

Although the lithium content in the crystal of GSSG lithium salt varies depending on the number of hydrated water contained in the crystal, it can be confirmed that when the crystal of GSSG lithium salt is a crystal of trihydrate, the crystal of GSSG dilithium salt is a crystal of dilithium salt, by a lithium content in the crystal of usually 2.2±1.0 wt %, preferably 2.2±0.7 wt %, and most preferably 2.2±0.5 wt %.

It can be confirmed that the crystal of GSSG dilithium salt is a crystal of trihydrate, by a water content in the crystal of usually 8.0±1.5 wt %, preferably 8.0±1.2 wt %, and most preferably 8.0±1.0 wt % as determined by the Karl-Fischer method or thermogravimetry differential thermal analysis.

The measurement of water content by the Karl-Fischer method may be performed, for example, in the same manner as in 1-1 described above.

Examples of the crystal of GSSG dilithium salt include a crystal having peaks at diffraction angle 2θ(°) described in the following (vii) in powder X-ray diffraction with CuKα as the X-ray source. A crystal having peaks at diffraction angles 2θ(°) described in the following (vii) and (viii) is preferred, and a crystal having peaks at diffraction angles 2θ (°) described in the following (vii), (viii) and (ix) is more preferred.
(vii) 18.9±0.2°, preferably ±0.1°; 19.3±0.2°, preferably ±0.1°; 20.1±0.2°, preferably ±0.1°; 20.5±0.2°, preferably ±0.1°; and 23.5±0.2°, preferably ±0.1°.
(viii) 24.6±0.2°, preferably ±0.1°; 21.3±0.2°, preferably ±0.1°; 20.3±0.2°, preferably ±0.1°; 25.9±0.2°, preferably ±0.1°; and 20.9±0.2°, preferably ±0.1°.
(ix) 24.0±0.2°, preferably ±0.1°; 4.6±0.2°, preferably ±0.1°; 26.2±0.2°, preferably ±0.1°; 26.5±0.2°, preferably ±0.1° and 22.2±0.2°, preferably ±0.1°.

Figure 5:
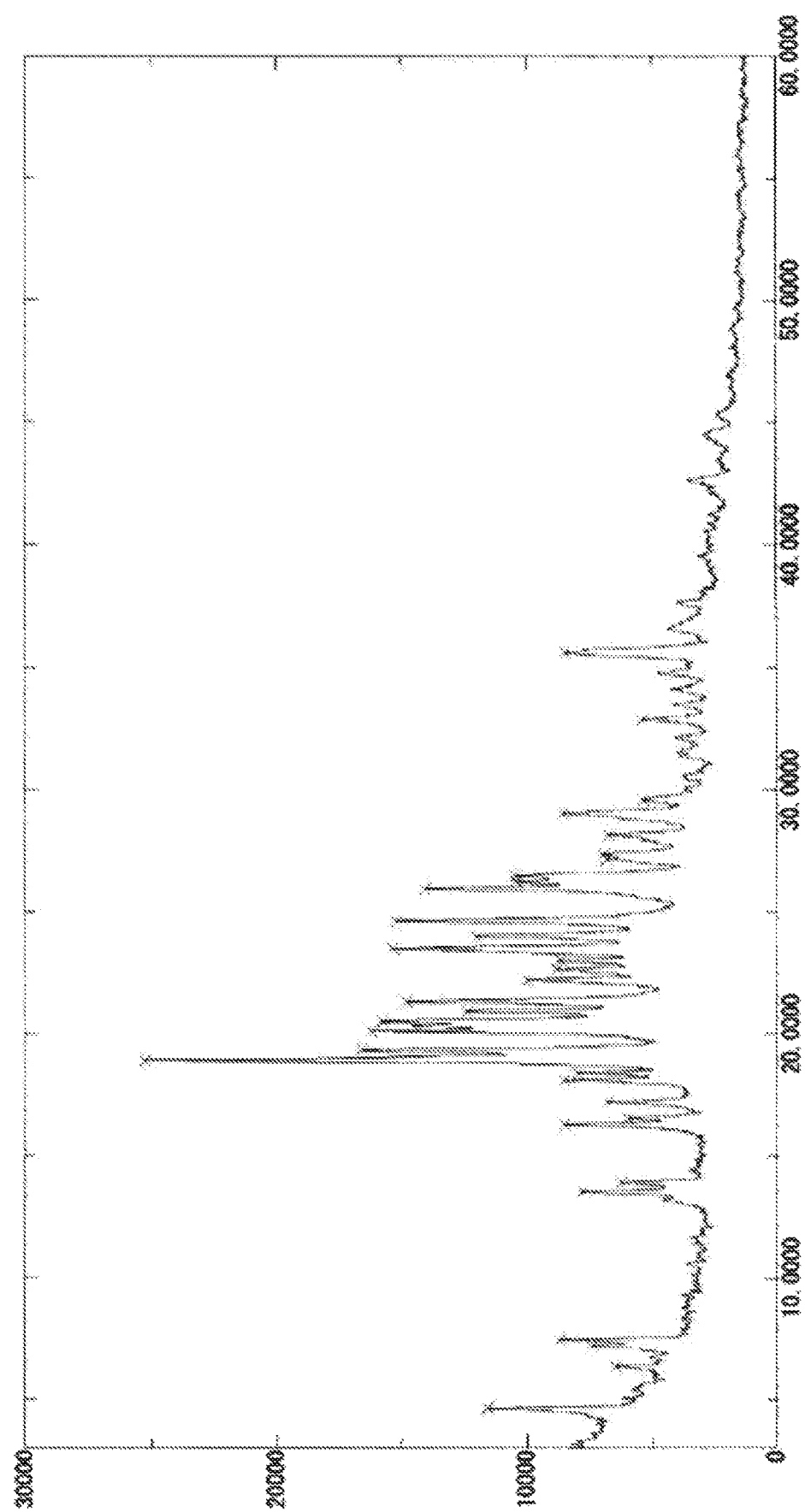
FIG. 5 illustrates the results of powder X-ray diffraction of a crystal of GSSG dilithium salt trihydrate obtained in Example 3. The vertical axis represents intensity (cps), and the horizontal axis represents diffraction angle 2θ(°).
Figure 6:
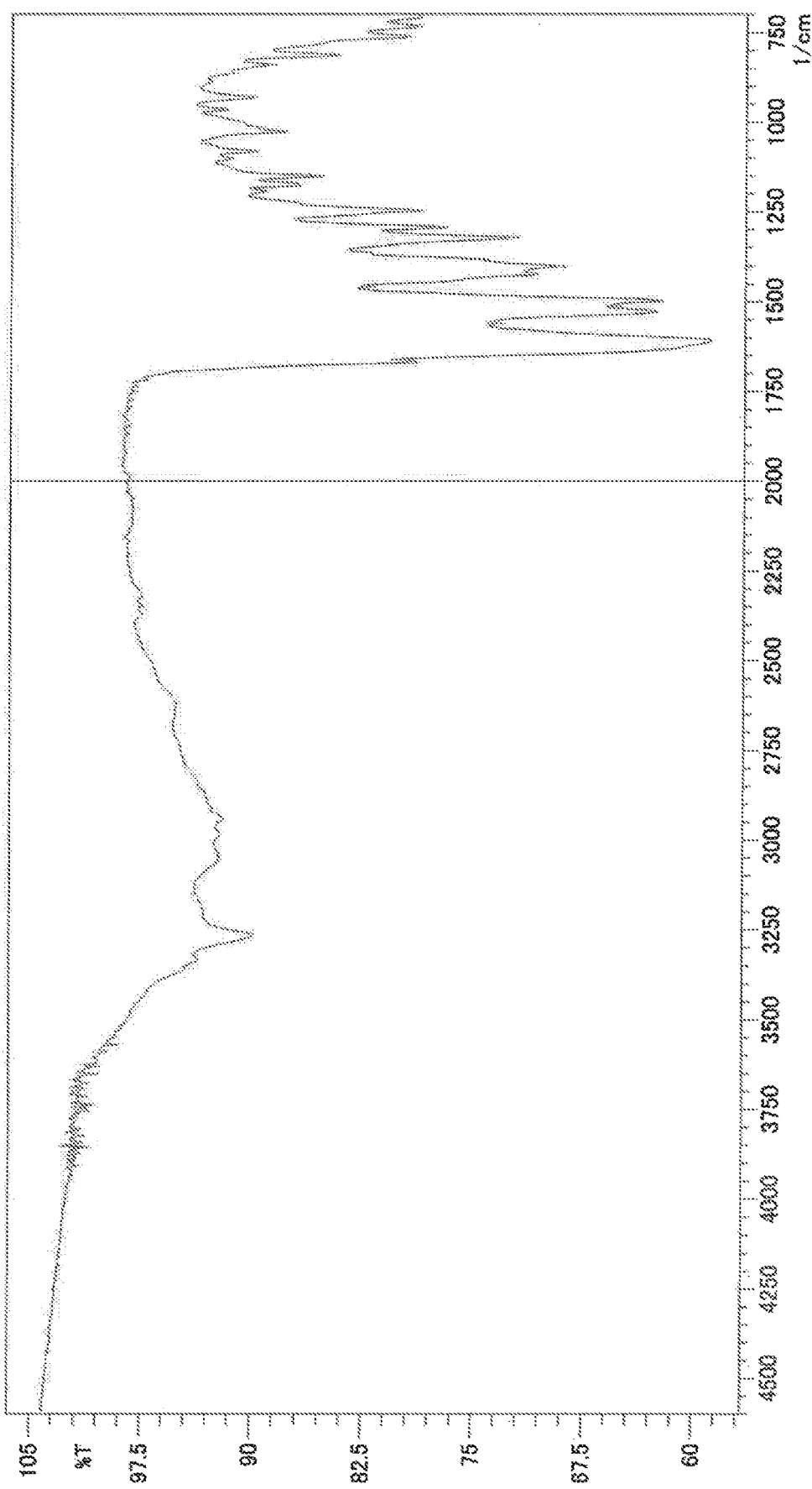
FIG. 6 illustrates the results of infrared spectroscopic (IR) analysis of a crystal of GSSG dilithium salt trihydrate obtained in Example 3. The vertical axis represents transmittance of light (% T), and the horizontal axis represents wavenumber (cm$^{-1}$).

Specific examples of the crystal of GSSG dilithium salt include a crystal of GSSG dilithium salt trihydrate of which powder X-ray diffraction pattern with use of CuKα as the X-ray source is specified by the pattern shown in FIG. 5 and the diffraction angle values described in Table 3, or a crystal of GSSG dilithium salt trihydrate having an infrared absorption spectrum shown in FIG. 6 in infrared spectroscopic (IR) analysis.

The infrared spectroscopic (IR) analysis may be performed, for example, in the same manner as in 1-1 described above.

1-4. Crystal of GSSG Diammonium Salt

It can be confirmed that the crystal of GSSG diammonium salt is a crystal of GSSG crystals by, for example, the same analysis using HPLC as in 1-1 described above.

It can be also confirmed that the crystal is a crystal of GSSG diammonium salt, by the same powder X-ray diffraction analysis as in 1-1 described above.

Although the crystal of GSSG diammonium salt may be a crystal of anhydrate or a crystal of hydrate, preferred examples include a crystal of hydrate and more preferred examples include a crystal of trihydrate.

Specific examples of the crystal of such a trihydrate include a crystal of GSSG diammonium salt trihydrate represented by composition formula $[C_{20}H_{30}N_6O_{12}S_2(NH_4)_2]3H_2O$.

It can be confirmed that the crystal of GSSG diammonium salt is a crystal of ammonium salt, through measurement of the ammonium content in the crystal.

The ammonium content may be confirmed by, for example, analysis using HPLC.

Examples of the analysis conditions in the analysis using HPLC include the following conditions.
Column: YMC-PACK AQ, diameter 6.0×150 mm (particle size: 5 μm, pore diameter: 12 nm)
Column temperature: 40° C.
Mobile phase: In 4000 mL of water, 14.7 g of sodium citrate dihydrate and 7.1 g of anhydrous sodium sulfate are dissolved, and then the pH is adjusted to 3.8 with concentrated sulfuric acid. Thereafter, 15.0 g of sodium lauryl sulfate and 600 mL of 1-propanol are added, and the solution is diluted in a measuring cylinder to 5000 mL with water for use as a mobile phase.
Flow rate of mobile phase: 1.2 mL/min
Reaction liquid: In 600 mL of water, 18.5 g of boric acid and 10.0 g of sodium hydroxide are dissolved, and after addition of 4.2 mL of Briji-35, the solution is diluted in a measuring cylinder to 1000 mL with water. Thereafter, 0.6 g of O-phthalaldehyde and 4.6 g of N-acetyl-L-cysteine are added and dissolved to obtain a reaction liquid. Flow rate of reaction liquid: 0.4 mL/min
Detector: Fluorescence detector (excitation wavelength: 355 nm, fluorescence wavelength: 455 nm)

Although the ammonium content in the crystal of GSSG diammonium salt varies depending on the number of hydrated water contained in the crystal, it can be confirmed that when the crystal of GSSG diammonium salt is a crystal of trihydrate, the crystal of GSSG diammonium salt is a crystal of diammonium salt, by an ammonium content in the crystal of usually 5.3±1.0 wt %, preferably 5.3±0.7 wt %, and most preferably 5.3±0.5 wt %.

It can be confirmed that the crystal of GSSG diammonium salt is a crystal of trihydrate, by a water content in the crystal of usually 7.7±1.0 wt %, preferably 7.7±0.7 wt %, and most preferably 7.7±0.5 wt % by the Karl-Fischer method or thermogravimetry differential thermal analysis.

The measurement of water content by the Karl-Fischer method may be performed in the same manner as in 1-1 described above.

Examples of the crystal of GSSG diammonium salt include a crystal having peaks at diffraction angle 2θ(°) described in the following (x) in powder X-ray diffraction with CuKα as the X-ray source. A crystal having peaks at diffraction angles 2θ(°) described in the following (x) and (xi) is preferred, and a crystal having peaks at diffraction angles 2θ(°) described in the following (x), (xi) and (xii) is more preferred.

(x) 15.8±0.2°, preferably ±0.1°; 24.6±0.2°, preferably ±0.1°; 24.3±0.2°, preferably ±0.1°; 10.5±0.2°, preferably ±0.1°; and 20.9±0.2°, preferably ±0.1°.

(xi) 18.5±0.2°, preferably ±0.1°; 14.7±0.2°, preferably ±0.1°; 22.2±0.2°, preferably ±0.1°; 5.7±0.2°, preferably ±0.1°; and 16.7±0.2°, preferably ±0.1°.

(xii) 19.5±0.2°, preferably ±0.1°; 17.1±0.2°, preferably ±0.1°; 15.2±0.2°, preferably ±0.1°; 23.8±0.2°, preferably ±0.1° and 8.3±0.2°, preferably ±0.1°.

Figure 7:
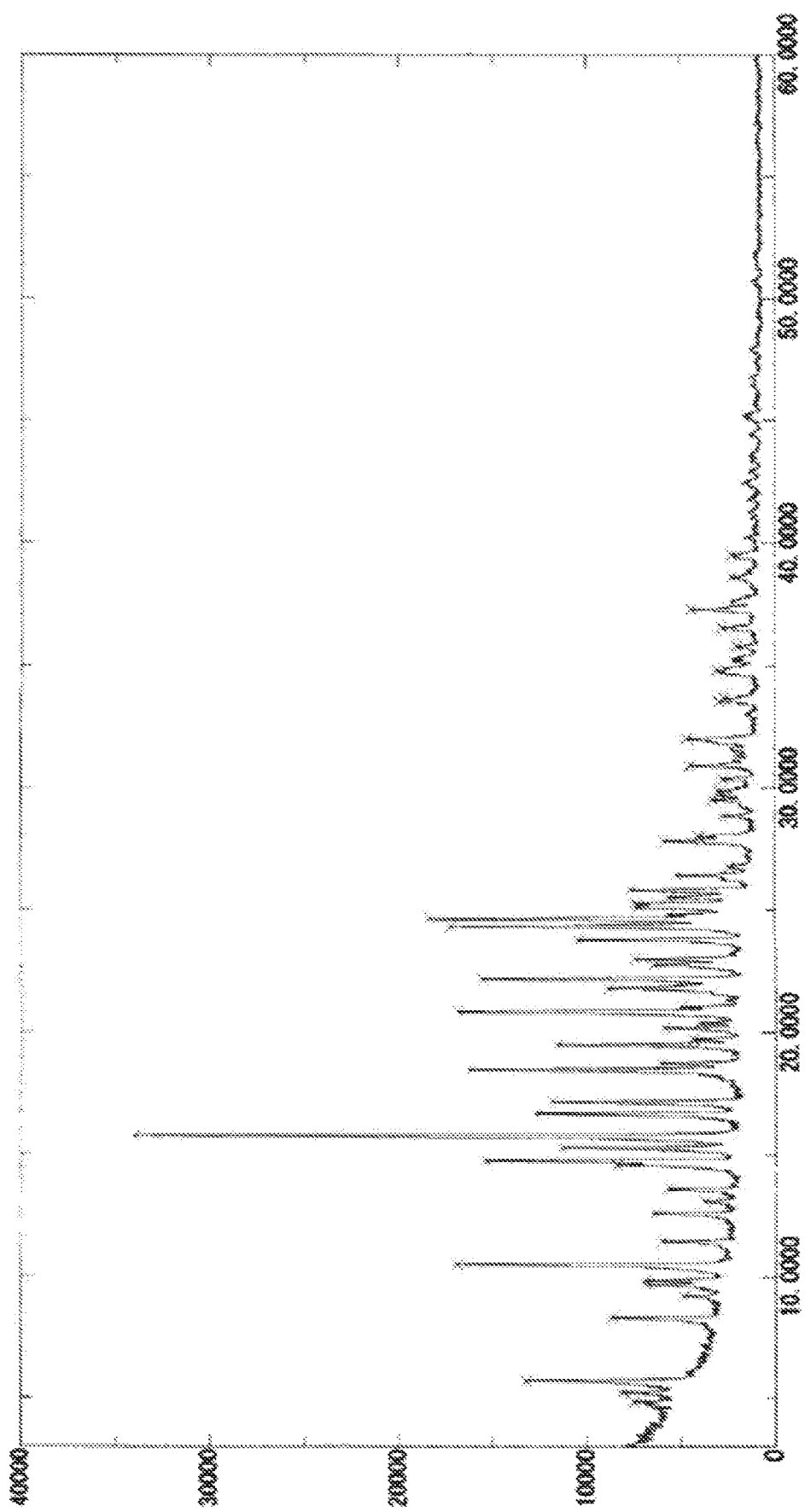
FIG. 7 illustrates the results of powder X-ray diffraction of a crystal of GSSG diammonium salt trihydrate obtained in Example 4. The vertical axis represents intensity (cps), and the horizontal axis represents diffraction angle 2θ(°).
Figure 8:
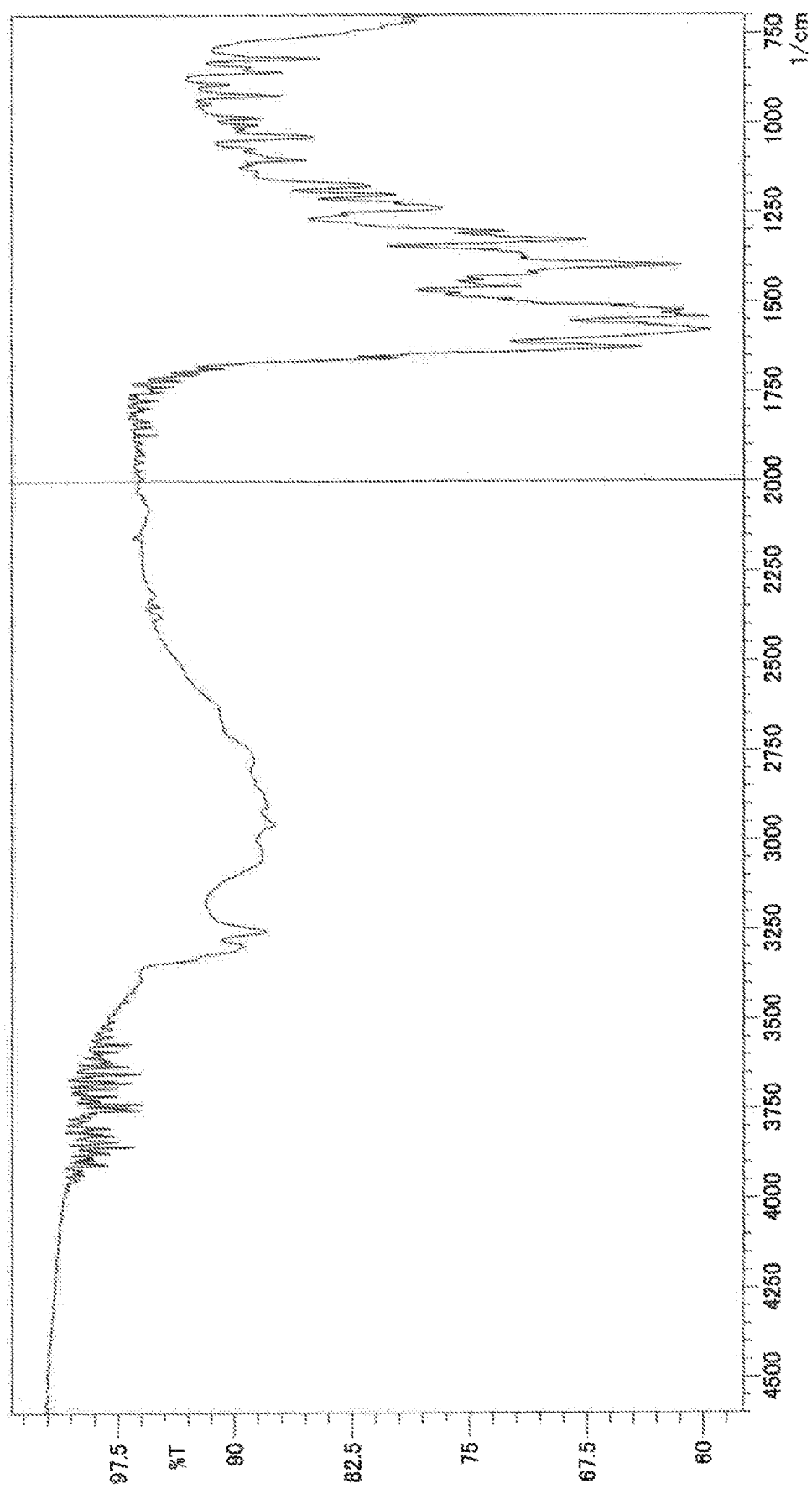
FIG. 8 illustrates the results of infrared spectroscopic (IR) analysis of a crystal of GSSG diammonium salt trihydrate obtained in Example 4. The vertical axis represents transmittance of light (% T), and the horizontal axis represents wavenumber (cm$^{-1}$).

Specific examples of the crystal of GSSG diammonium salt include a crystal of GSSG diammonium salt trihydrate of which powder X-ray diffraction pattern with use of CuKα as the X-ray source is specified by the pattern shown in FIG. 7 and the diffraction angle values described in Table 4, or a crystal of GSSG diammonium salt trihydrate having an infrared absorption spectrum shown in FIG. 8 in infrared spectroscopic (IR) analysis.

The infrared spectroscopic (IR) analysis may be performed, for example, in the same manner as in 1-1 described above.

2. Method of Producing a Crystal of the Present Invention

The method of producing a crystal of the present invention is a method described in the following 2-1 or 2-2.

2-1. Method 1 of Producing a Crystal of the Present Invention

The method of producing a crystal of the present invention is a method of producing a crystal of GSSG dication salt comprising a step of leaving a non-crystalline amorphous GSSG dication salt standing still for 48 hours or more.

The non-crystalline amorphous GSSG dication salt can be acquired by freeze-drying an aqueous solution of GSSG dissolving a cation-containing compound.

The GSSG contained in the aqueous solution of GSSG dissolving a cation-containing compound may be produced by any of production methods such as a fermentation method, an enzyme method, an extraction method from natural products and a chemical synthesis method, and examples thereof include a crystal of GSSG monohydrate prepared in accordance with the method of Patent Document 1 and a crystal of GSSG hexahydrate prepared in accordance with the method of Patent Document 2.

When the aqueous solution of GSSG dissolving a cation-containing compound contains a solid that hinders crystallization, the solid can be removed by centrifugation, filtration, or a ceramic filter.

When the aqueous solution of GSSG dissolving a cation-containing compound contains water-soluble impurities and salts that hinder crystallization, the water-soluble impurities and salts can be removed by passing the solution through a column packed with an ion exchange resin or the like.

When the aqueous solution of GSSG dissolving a cation-containing compound contains hydrophobic impurities that hinder crystallization, the hydrophobic impurities can be removed by passing the solution through a column packed with a synthetic adsorption resin, an activated carbon or the like.

It is preferable that the concentration of GSSG in the aqueous solution of GSSG dissolving a cation-containing compound be adjusted to 5 to 100 g/L, preferably 10 to 75 g/L, and more preferably 20 to 50 g/L, for use.

Specific examples of the cation-containing compound include a sodium-containing compound, a potassium-containing compound, a lithium-containing compound, and an ammonium-containing compound.

Examples of the sodium-containing compound include a basic compound such as sodium hydroxide, or a salt such as a carbonate of sodium, a sulfate of sodium, a nitrate of sodium, and a chloride of sodium. Examples of the salt include sodium carbonate, sodium sulfate, sodium nitrate, and sodium chloride.

In the case of using a basic compound as the sodium-containing compound, the pH of the aqueous solution of GSSG is adjusted using the basic compound, so that an aqueous solution of GSSG dissolving the sodium-containing compound, having a pH of usually of 4.0 to 10.0, preferably 4.5 to 9.5, and most preferably 5.0 to 9.0, can be acquired.

Examples of the potassium-containing compound include a basic compound such as potassium hydroxide, or a salt such as a carbonate of potassium, a sulfate of potassium, a nitrate of potassium, and a chloride of potassium. Examples of the salt include potassium carbonate, potassium sulfate, potassium nitrate, and potassium chloride.

In the case of using a basic compound as the potassium-containing compound, the pH of the aqueous solution of GSSG is adjusted using the basic compound, so that an aqueous solution of GSSG dissolving the potassium-containing compound, having a pH of usually of 4.0 to 10.0, preferably 4.5 to 9.5, and most preferably 5.0 to 9.0, can be acquired.

Examples of the lithium-containing compound include a basic compound such as lithium hydroxide, or a salt such as a carbonate of lithium, a sulfate of lithium, a nitrate of lithium, and a chloride of lithium. Examples of the salt include lithium carbonate, lithium sulfate, lithium nitrate, and lithium chloride.

In the case of using a basic compound as the lithium-containing compound, the pH of the aqueous solution of GSSG is adjusted using the basic compound, so that an aqueous solution of GSSG dissolving the lithium-containing compound, having a pH of usually of 4.0 to 10.0, preferably 4.5 to 9.5, and most preferably 5.0 to 9.0, can be acquired.

Examples of the ammonium-containing compound include a basic compound such as ammonia, or a salt such as a carbonate of ammonia, a sulfate of ammonia, a nitrate of ammonia, and a chloride of ammonia. Examples of the salt include ammonium carbonate, ammonium sulfate, ammonium nitrate, and ammonium chloride.

In the case of using a basic compound as the ammonium-containing compound, the pH of the aqueous solution of GSSG is adjusted using the basic compound, so that an aqueous solution of GSSG dissolving the ammonium-containing compound, having a pH of usually of 4.0 to 10.0, preferably 4.5 to 9.5, and most preferably 5.0 to 9.0, can be acquired.

In the method of 2-1, in the case of using a sodium-containing compound as the cation-containing compound, the resulting non-crystalline amorphous GSSG dication salt is a non-crystalline amorphous GSSG disodium salt.

In the method of 2-1, in the case of using a potassium-containing compound as the cation-containing compound, the resulting non-crystalline amorphous GSSG dication salt is a non-crystalline amorphous GSSG dipotassium salt.

In the method of 2-1, in the case of using a lithium-containing compound as the cation-containing compound, the resulting non-crystalline amorphous GSSG dication salt is a non-crystalline amorphous GSSG dilithium salt.

In the method of 2-1, in the case of using an ammonium-containing compound as the cation-containing compound, the resulting non-crystalline amorphous GSSG dication salt is a non-crystalline amorphous GSSG diammonium salt.

The time required for freeze-drying the aqueous solution of GSSG dissolving a cation-containing compound is usually 24 hours or more, preferably 48 hours or more, and more preferably 72 hours or more.

The non-crystalline amorphous GSSG dication salt acquired by the method described above is left standing still for 48 hours or more to produce a crystal of GSSG dication salt.

In the step of leaving the non-crystalline amorphous GSSG dication salt standing still, the time required for standing still is usually 48 hours or more, preferably 60 hours or more, and more preferably 72 hours or more.

In the step of leaving the non-crystalline amorphous GSSG dication salt, the temperature in the environment is usually 10 to 70° C., preferably 20 to 60° C., and more preferably 30 to 50° C.

In the step of leaving the non-crystalline amorphous GSSG dication salt, the relative humidity in the environment is usually 40 to 100%, preferably 50 to 95%, and more preferably 60 to 90%.

In the method of 2-1, in the case of using a non-crystalline amorphous GSSG disodium salt as the non-crystalline amorphous material, the resulting crystal of GSSG dication salt is a crystal of GSSG disodium salt, more specifically a crystal of GSSG disodium salt hexahydrate.

In the method of 2-1, in the case of using a non-crystalline amorphous GSSG dipotassium salt as the non-crystalline amorphous material, the resulting crystal of GSSG dication salt is a crystal of GSSG dipotassium salt, more specifically a crystal of GSSG dipotassium salt trihydrate.

In the method of 2-1, in the case of using a non-crystalline amorphous GSSG dilithium salt as the non-crystalline amorphous material, the resulting crystal of GSSG dication salt is a crystal of GSSG dilithium salt, more specifically a crystal of GSSG dilithium salt trihydrate.

In the method of 2-1, in the case of using a non-crystalline amorphous GSSG diammonium salt as the non-crystalline amorphous material, the resulting crystal of GSSG dication salt is a crystal of GSSG diammonium salt, more specifically a crystal of GSSG diammonium salt trihydrate.

The purity of the crystal of GSSG dication salt acquired by the method described above may be 95% or more, preferably 96% or more, more preferably 97% or more, and most preferably 97.5% or more.

The purity of the crystal of GSSG dication salt can be confirmed, for example, by the same analysis using HPLC as in 1-1 described above.

Specific examples of the crystal of GSSG cation salt which can be produced by the production method described above include a crystal of GSSG disodium salt hexahydrate described in Example 1, a crystal of GSSG dipotassium salt trihydrate described in Example 2, a crystal of GSSG dilithium salt trihydrate described in Example 3 and a crystal of GSSG diammonium salt trihydrate described in Example 4.

2-2. Method 2 of Producing a Crystal of the Present Invention

Examples of the method of producing a crystal of the present invention other than the method described in 2-1 include a method of producing a crystal of GSSG dication salt comprising a step of dropping or adding alcohol to an aqueous solution of GSSG dissolving a cation-containing compound, a step of adding a crystal of GSSG dication salt as a seed crystal to the aqueous solution to precipitate the crystal of GSSG dication salt, and a step of collecting the crystal of GSSG dication salt from the aqueous solution.

As GSSG contained in the aqueous solution of GSSG dissolving a cation-containing compound, the same GSSG as in 2-1 described above can be used.

In each of the cases where a solid matter which hinders crystallization is contained in the aqueous solution of GSSG dissolving a cation-containing compound, where water-soluble impurities and salts which hinder crystallization are contained in the aqueous solution of GSSG dissolving a cation-containing compound, and where hydrophobic impurities which hinder crystallization are contained in the aqueous solution of GSSG dissolving a cation-containing compound, the same treatment as in 2-1 described above may be performed.

It is preferable that the concentration of GSSG in the aqueous solution of GSSG dissolving a cation-containing compound be adjusted to 200 g/L or more, preferably 250 g/L or more, and more preferably 300 g/L or more for use.

Specific examples of the cation-containing compound include a sodium-containing compound, a potassium-containing compound, a lithium-containing compound and an ammonium-containing compound.

As the sodium-containing compound, the potassium-containing compound, the lithium-containing compound and the ammonium-containing compound, the same compounds as in 2-1 described above may be used.

In the case of using each of the basic compounds as the cation-containing compound, the basic compound is used to adjust the pH of an aqueous solution of GSSG using the basic compound in the same manner as in 2-1 described above, so that the aqueous solution of GSSG, having a pH of usually 4.0 to 10.0, preferably 4.5 to 9.5, and most preferably 5.0 to 9.0, can be acquired.

Examples of the alcohol to be added or dropped to the aqueous solution include preferably C1 to C6 alcohols, more preferably C1 to C3 alcohols, still more preferably alcohols selected from the group consisting of methanol, ethanol, n-propanol and isopropanol, furthermore preferably methanol or ethanol, and most preferably methanol.

The alcohol may be a mixture of a plurality of alcohols, or a mixture of an alcohol and another organic solvent or water.

When the alcohol is a mixture of an alcohol and water, the water content may be 40 wt % or less, preferably 20 wt % or less, more preferably 10 wt % or less, and most preferably 5 wt % or less.

In the step of adding or dropping an alcohol to the aqueous solution, the temperature of the aqueous solution may be usually 0 to 80° C., preferably 5 to 70° C., more preferably 10 to 60° C., still more preferably 15 to 50° C., and most preferably 20 to 40° C.

In the step of adding or dropping an alcohol to the aqueous solution, the liquid volume of the alcohol to be dropped or added may be 1 to 8 times the volume of the aqueous solution, preferably 1 to 6 times the volume, and most preferably 1 to 5 times the volume.

In the step of adding or dropping an alcohol to the aqueous solution, the time required for adding or dropping of the alcohol may be 15 minutes to 48 hours, preferably 30 minutes to 24 hours, and most preferably 1 to 12 hours.

In the method of 2-2, immediately before starting dropping or adding an alcohol to the aqueous solution of GSSG dissolving a cation-containing compound, or before precipitation of a crystal of GSSG dication salt after dropping or adding an alcohol to the aqueous solution, a seed crystal is added.

As the seed crystal, for example, a crystal of GSSG dication salt acquired in 2-1 or 2-2 may be used.

In the method of 2-2, in the case of using a sodium-containing compound as the cation-containing compound, and a crystal of GSSG disodium salt hexahydrate as the seed crystal, the resulting crystal of GSSG dication salt is a crystal of GSSG disodium salt hexahydrate.

In the method of 2-2, in the case of using a potassium-containing compound as the cation-containing compound, and a crystal of GSSG dipotassium salt trihydrate as the seed crystal, the resulting crystal of GSSG dication salt is a crystal of GSSG dipotassium salt trihydrate.

In the method of 2-2, in the case of using a lithium-containing compound as the cation-containing compound, and a crystal of GSSG dilithium salt trihydrate as the seed crystal, the resulting crystal of GSSG dication salt is a crystal of GSSG dilithium salt trihydrate.

In the method of 2-2, in the case of using an ammonium-containing compound as the cation-containing compound, and a crystal of GSSG diammonium salt trihydrate as the seed crystal, the resulting crystal of GSSG dication salt is a crystal of GSSG diammonium salt trihydrate.

The seed crystal is added, such that the content thereof in the aqueous solution of GSSG dissolving a cation-containing compound is usually 0.001 to 50 g/L, preferably 0.01 to 10 g/L, and more preferably 0.1 to 5 g/L.

The seed crystal may be added, for example, immediately after completion of addition or dropping of an alcohol.

After precipitation of the crystal of GSSG dication salt by the method described above, the precipitated crystal may be matured for usually 1 to 48 hours, preferably 1 to 36 hours, and most preferably 1 to 24 hours.

"Maturing a crystal" means that the crystal is grown by stopping the step of precipitating a crystal of GSSG dication salt.

"Growing a crystal" means that a crystal is grown based on the precipitated crystal.

Although maturing of a crystal is performed mainly to grow the crystal, precipitation of a new crystal may occur in parallel with the crystal growth.

Stopping the step of precipitating a crystal of GSSG diction salt, for example, means that addition or dropping of an alcohol is suspended.

After maturing of the crystal, the step of precipitating a crystal of GSSG dication salt may be resumed.

In the step of collecting a crystal of GSSG dication salt, for example, filtration, pressure filtering, suction filtering and centrifugation may be performed. Furthermore, in order to reduce adhesion of mother liquid to the crystal for improvement in the quality of the crystal, the crystal may be appropriately washed after collection of the crystal.

As the liquid for washing the crystal, for example, a liquid obtained by mixing one or more kinds selected from the group consisting of water, methanol, ethanol, acetone, n-propanol and isopropanol at an arbitrary ratio may be used.

The crystal of the present invention can be obtained by drying a wet crystal obtained in this matter.

The drying conditions are not particularly limited as long as the crystal form of GSSG dication salt can be maintained, and drying under reduced pressure, vacuum drying, fluidized bed drying, ventilation drying, or the like may be applied.

The drying temperature may be in any range as long as adhesive moisture or solution can be removed, and may be preferably 80° C. or less, more preferably 70° C. or less, and most preferably 60° C. or less.

The drying time may be in any range as long as adhesive moisture or solution can be removed, and may be preferably 1 to 60 hours, and more preferably 1 to 48 hours.

The purity of the crystal of GSSG dication salt acquired by the method described above may be 95% or more, preferably 96% or more, more preferably 97% or more, and most preferably 97.5% or more.

The purity of the crystal of GSSG dication salt can be confirmed, for example, by the same analysis using HPLC as in 1-1 described above.

Specific examples of the crystal of GSSG dication salt which can be produced by the production method described above include a crystal of GSSG disodium salt hexahydrate of which powder X-ray diffraction pattern with use of CuKα as the X-ray source is specified by the pattern shown in FIG. 1 and the diffraction angle values described in Table 1, a crystal of GSSG dipotassium salt trihydrate specified by the pattern shown in FIG. 3 and the diffraction angle values described in Table 3, a crystal of GSSG dilithium salt trihydrate specified by the pattern shown in FIG. 5 and the diffraction angle values described in Table 5, and a crystal of GSSG diammonium salt trihydrate specified by the pattern shown in FIG. 7 and the diffraction angle values described in Table 7.

Specific examples of the crystal of GSSG dication salt which can be produced by the production method described above also include a crystal of GSSG disodium salt hexahydrate having an infrared absorption spectrum shown in FIG. 2, a crystal of GSSG dipotassium salt trihydrate having an infrared absorption spectrum shown in FIG. 4, a crystal of GSSG dilithium salt trihydrate having an infrared absorption spectrum shown in FIG. 6, and a crystal of GSSG diammonium salt trihydrate having an infrared absorption spectrum shown in FIG. 8 when subjected to infrared spectroscopic (IR) analysis.

EXAMPLES

Examples will be described as below, though the present invention is not limited to the following Examples.

In the following Examples, each analysis was performed using the following apparatuses under the following conditions unless otherwise noted.

Powder X-ray diffraction analysis was performed using a powder X-ray diffractometer (XRD) Ultima IV (manufactured by Rigaku Corporation) with CuKα as the X-ray source in accordance with the attached instruction manual.

HPLC analysis for identifying GSSG was performed as follows.

Column: Inertsil ODS-3 (150 mm×3 mm ID)
Column temperature: 35° C.
Mobile phase: In 1000 mL of water, 6.8 g of potassium dihydrogen phosphate and 2.0 g of sodium 1-heptanesulfonate were dissolved, and then phosphoric acid was added thereto to adjust the pH to 3.0. To 970 mL of the solution, 30 mL of methanol was added for use as mobile phase.
Flow rate: 0.5 mL/min
Detector: UV detector (wavelength: 210 nm)
Retention time: about 15 minutes HPLC analysis for identifying ammonia was performed as follows.

Column: YMC-PACK AQ, diameter 6.0×150 mm (particle size: 5 μm, pore diameter: 12 nm)
Column temperature: 40° C.
Mobile phase: In 4000 mL of water, 14.7 g of sodium citrate dihydrate and 7.1 g of anhydrous sodium sulfate were dissolved, and then the pH was adjusted to 3.8 with concentrated sulfuric acid. Thereafter, 15.0 g of sodium lauryl sulfate and 600 mL of 1-propanol were added, and the solution was diluted in a measuring cylinder to 5000 mL with water for use as a mobile phase.

Flow rate of mobile phase: 1.2 mL/min
Reaction liquid: In 600 mL of water, 18.5 g of boric acid and 10.0 g of sodium hydroxide were dissolved, and after addition of 4.2 mL of Briji-35, the solution was diluted in a measuring cylinder to 1000 mL with water. Thereafter, 0.6 g of O-phthalaldehyde and 4.6 g of N-acetyl-L-cysteine were added and dissolved to obtain a reaction liquid.
Flow rate of reaction liquid: 0.4 mL/min
Detector: Fluorescence detector (excitation wavelength: 355 nm, fluorescence wavelength: 455 nm)
Retention time: about 10 minutes The water content measurement was performed by using MKA-510N/MKS-510N (manufactured by Kyoto Electronics Manufacturing Co., Ltd.) in accordance with the attached instruction manual.

Atomic absorption analysis was performed by using an atomic absorption photometer Z-2310 (manufactured by Hitachi High-Technologies Corporation) in accordance with the attached instruction manual.

IR analysis was performed by using FUR-8400 type (manufactured by Shimadzu Corporation) in accordance with the attached instruction manual.

Example 1

(1) Acquisition of crystal of GSSG disodium salt hexahydrate—1

In water, 25 g of a crystal of GSSG monohydrate prepared in accordance with the method of Patent Document 1 was dissolved, and then pH was adjusted to 6.5 using sodium hydroxide. The solution was diluted with water to prepare 250 mL of an aqueous solution containing 30 g/L of GSSG. The aqueous solution was filtrated with a 0.45 μm filter, and then freeze-dried for 72 hours to obtain a whitish transparent powder. In powder X-ray diffraction measurement of the powder, no X-ray diffraction peak was confirmed, so that the powder was found to be a non-crystalline amorphous material. From the results of HPLC analysis and sodium content measurement of the powder, the powder was found to be GSSG disodium salt. From the above, the powder was found to be a non-crystalline amorphous GSSG disodium salt.

The non-crystalline amorphous GSSG disodium salt acquired was spread on a petri dish and left standing still for 3 days to be exposed to an environment with a relative humidity of 75% at 40° C., so that a crystal precipitated.

(2) Acquisition of crystal of GSSG disodium salt hexahydrate—2

In water, 120 g of a crystal of GSSG hexahydrate prepared in accordance with the method of Patent Document 2 was dissolved, and the pH was adjusted to 6.2 using sodium hydroxide, so that 333 mL of a solution was obtained. To the aqueous solution, 400 mL of methanol was added over a time of 1 hour, and 0.1 g of the crystal acquired in Example 1 (1) described above was added as a seed crystal to precipitate a crystal. The crystal slurry was then cooled to 30° C., and stirred for 24 hours to mature the crystal, which was then filtrated and dried at 30° C. under reduced pressure to obtain 20 g of the crystal.

As a result of powder X-ray diffraction of the resulting crystal, the powder X-ray diffraction pattern of the crystal was as shown in FIG. 1. As a result of powder X-ray diffraction, the diffraction angles of peaks having a relative intensity ratio (I/I₀) of 10 or more are shown in Table 1. In the table, "2θ" represents diffraction angle 2θ(°) and "relative intensity" represents relative intensity ratio (I/I₀).

TABLE 1

| 2θ | Relative intensity |
|---|---|
| 6.4 | 58 |
| 7.8 | 45 |
| 9.0 | 37 |
| 11.5 | 30 |
| 11.7 | 31 |
| 12.7 | 57 |
| 14.2 | 37 |
| 15.3 | 31 |
| 15.7 | 33 |
| 16.6 | 36 |
| 18.5 | 100 |
| 18.9 | 61 |
| 19.4 | 54 |
| 19.9 | 51 |
| 20.2 | 38 |
| 20.7 | 73 |
| 21.3 | 68 |
| 22.0 | 53 |
| 22.5 | 58 |
| 22.8 | 49 |
| 23.2 | 66 |
| 23.6 | 62 |
| 24.4 | 46 |
| 25.6 | 49 |
| 26.2 | 42 |
| 27.1 | 42 |
| 28.1 | 36 |
| 29.7 | 35 |

The IR analysis result of the resulting crystal was as shown in FIG. 2.

As the HPLC analysis result, the crystal was found to be a crystal of GSSG. The sodium content of the crystal measured in atomic absorption analysis was 7.1 wt % (in terms of anhydrate), which approximately coincided with the theoretical value of disodium salt (7.0 wt %). The water content in the crystal was 13.3 wt %, which approximately coincided with the theoretical value of hexahydrate (14.1 wt %).

From the above, the crystal was found to be a crystal of GSSG disodium salt hexahydrate.

The various physical properties of the crystal are shown in Table 2. The pH of an aqueous solution of 25 g/L of GSSG disodium salt hexahydrate was measured. Measurement of melting point was performed by using Melting Point M-565 (manufactured by BUeCHI) under conditions at 50° C. to 200° C., 0.5° C./min, in accordance with the attached instruction manual.

TABLE 2

| | |
|---|---|
| Water content (wt %) | 13.3 |
| Sodium content (wt %) | 7.1 |
| Melting point (° C.) | 182.4 |
| pH | 6.1 |

The crystal acquired in Example 1 (1) used as a seed crystal was also subjected to powder X-ray diffraction measurement, and the resulting peak pattern coincided with the pattern shown in FIG. 1. It was therefore confirmed that the crystal was a crystal of GSSG disodium salt hexahydrate.

Example 2

(1) Acquisition of GSSG Dipotassium Salt Trihydrate—1

In water, 25 g of a crystal of GSSG monohydrate prepared in accordance with the method of Patent Document 1 was dissolved, and then pH was adjusted to 6.5 using potassium hydroxide. The solution was diluted with water to prepare 250 mL of an aqueous solution containing 30 g/L of GSSG. The aqueous solution was filtrated with a 0.45 µm filter, and then freeze-dried for 72 hours to obtain a whitish transparent powder. In powder X-ray diffraction measurement of the powder, no X-ray diffraction peak was identified, so that the powder was found to be a non-crystalline amorphous material. From the results of HPLC analysis and potassium content measurement of the powder, the powder was found to be GSSG dipotassium salt. From the above, the powder was found to be a non-crystalline amorphous GSSG dipotassium salt.

The non-crystalline amorphous GSSG dipotassium salt acquired was spread on a petri dish and left standing still for 2 days to be exposed to an environment with a relative humidity of 75% at 40° C., so that a crystal precipitated.

(2) Acquisition of GSSG Dipotassium Salt Trihydrate—2

In water, 120 g of a crystal of GSSG hexahydrate prepared in accordance with the method of Patent Document 2 was dissolved, and the pH was adjusted to 6.2 using potassium hydroxide, so that 333 mL of a solution was obtained. To the aqueous solution, 400 mL of methanol was added over a time of 1 hour, and 0.1 g of the crystal acquired in Example 2 (1) described above was added as a seed crystal to precipitate a crystal. The crystal slurry was then cooled to 30° C., and stirred for 24 hours to mature the crystal, which was then filtrated and dried at 30° C. under reduced pressure to obtain 20 g of the crystal.

As a result of powder X-ray diffraction of the resulting crystal, the powder X-ray diffraction pattern of the crystal was as shown in FIG. 3. As a result of powder X-ray diffraction, the diffraction angles of peaks having a relative intensity ratio ($I/I_0$) of 10 or more are shown in Table 3. In the table, "2θ" represents diffraction angle 2θ(°) and "relative intensity" represents relative intensity ratio ($I/I_0$).

TABLE 3

| 2θ | Relative intensity |
|---|---|
| 11.0 | 34 |
| 12.5 | 33 |
| 17.5 | 63 |
| 18.1 | 56 |
| 19.2 | 51 |
| 19.7 | 50 |
| 20.4 | 65 |
| 21.6 | 80 |
| 22.1 | 99 |
| 23.3 | 59 |
| 23.8 | 100 |
| 25.0 | 66 |
| 25.6 | 63 |
| 26.7 | 63 |
| 27.8 | 52 |
| 28.5 | 55 |
| 31.5 | 46 |
| 32.8 | 38 |
| 36.2 | 45 |

The IR analysis result of the resulting crystal was as shown in FIG. 4.

As the HPLC analysis result, the crystal was found to be a crystal of GSSG. The potassium content of the crystal measured in atomic absorption analysis was 10.3 wt % (in twits of anhydrate), which approximately coincided with the theoretical value of dipotassium salt (11.4 wt %). The water content in the crystal was 7.3 wt %, which approximately coincided with the theoretical value of trihydrate (7.3 wt %).

From the above, the crystal was found to be a crystal of GSSG dipotassium salt trihydrate.

The various physical properties of the crystal are shown in Table 4. The pH of an aqueous solution of 25 g/L of GSSG dipotassium salt trihydrate was measured. Measurement of melting point was performed by using Melting Point M-565 (manufactured by BUeCHI) under conditions at 50° C. to 200° C., 0.5° C./min, in accordance with the attached instruction manual.

TABLE 4

| Water content (wt %) | 7.3 |
|---|---|
| Potassium content (wt %) | 10.3 |
| Melting point (° C.) | 182.4 |
| pH | 6.1 |

The crystal acquired in Example 2 (1) used as a seed crystal was also subjected to powder X-ray diffraction measurement, and the resulting peak pattern coincided with the pattern shown in FIG. 3. It was therefore confirmed that the crystal was a crystal of GSSG dipotassium salt trihydrate.

Example 3

(1) Acquisition of GSSG Dilithium Salt Trihydrate—1

In water, 25 g of a crystal of GSSG hexahydrate prepared in accordance with the method of Patent Document 2 was dissolved, and then pH was adjusted to 6.2 using lithium hydroxide. The solution was diluted with water to prepare 250 mL of an aqueous solution containing 30 g/L of GSSG. The aqueous solution was filtrated with a 0.45 µm filter, and then freeze-dried for 72 hours to obtain a whitish transparent powder. In powder X-ray diffraction measurement of the powder, no X-ray diffraction peak was identified, so that the powder was found to be a non-crystalline amorphous material. From the results of HPLC analysis and lithium content measurement of the powder, the powder was found to be GSSG dilithium salt. From the above, the powder was found to be a non-crystalline amorphous GSSG dilithium salt.

The non-crystalline amorphous GSSG dilithium salt acquired was spread on a petri dish and left standing still for 2 days to be exposed to an environment with a relative humidity of 75% at 40° C., so that a crystal precipitated.

(2) Acquisition of GSSG Dilithium Salt Trihydrate—2

In water, 120 g of a crystal of GSSG hexahydrate prepared in accordance with the method of Patent Document 2 was dissolved, and the pH was adjusted to 6.2 using lithium hydroxide, so that 333 mL of a solution was obtained. To the aqueous solution, 400 mL of methanol was added over a time of 1 hour, and 0.1 g of the crystal acquired in Example 3 (1) described above was added as a seed crystal to precipitate a crystal. The crystal slurry was then cooled to 30° C., and stirred for 24 hours to mature the crystal, which was then filtrated and dried at 30° C. under reduced pressure to obtain 20 g of the crystal.

As a result of powder X-ray diffraction of the resulting crystal, the powder X-ray diffraction pattern of the crystal was as shown in FIG. 5. As a result of powder X-ray diffraction, the diffraction angles of peaks having a relative intensity ratio ($I/I_0$) of 10 or more are shown in Table 5. In the table, "2θ" represents diffraction angle 2θ(°) and "relative intensity" represents relative intensity ratio ($I/I_0$).

TABLE 5

| 2θ | Relative intensity |
|---|---|
| 4.6 | 46 |
| 6.4 | 26 |
| 7.2 | 30 |
| 7.5 | 35 |
| 13.5 | 31 |
| 13.9 | 26 |
| 16.3 | 34 |
| 16.6 | 24 |
| 17.2 | 27 |
| 18.1 | 34 |
| 18.4 | 32 |
| 18.9 | 100 |
| 19.3 | 66 |
| 20.1 | 65 |
| 20.3 | 58 |
| 20.5 | 63 |
| 20.9 | 50 |
| 21.3 | 59 |
| 22.2 | 40 |
| 22.6 | 36 |
| 23.0 | 35 |
| 23.5 | 61 |
| 24.0 | 48 |
| 24.6 | 61 |
| 25.9 | 56 |
| 26.2 | 42 |
| 26.5 | 42 |
| 27.2 | 28 |
| 27.4 | 28 |
| 28.2 | 27 |
| 29.2 | 34 |
| 29.6 | 22 |
| 32.8 | 22 |
| 35.6 | 34 |

The IR analysis result of the resulting crystal was as shown in FIG. 6.

As the HPLC analysis result, the crystal was found to be a crystal of GSSG. The lithium content of the crystal measured in atomic absorption analysis was 2.2 wt % (in terms of anhydrate), which approximately coincided with the theoretical value of dilithium salt (2.2 wt %). The water content in the crystal was 8.7 wt %, which approximately coincided with the theoretical value of trihydrate (8.0 wt %).

From the above, the crystal was found to be a crystal of GSSG dilithium salt trihydrate.

The various physical properties of the crystal are shown in Table 6. The pH of an aqueous solution of 25 g/L of GSSG dilithium salt trihydrate was measured. Measurement of melting point was performed by using Melting Point M-565 (manufactured by BUeCHI) under conditions at 50° C. to 200° C., 0.5° C./min, in accordance with the attached instruction manual.

TABLE 6

| | |
|---|---|
| Water content (wt %) | 8.7 |
| Lithium content (wt %) | 2.2 |
| Melting point (° C.) | 214.8 |
| pH | 6.4 |

The crystal acquired in Example 3 (1) used as a seed crystal was also subjected to powder X-ray diffraction measurement, and the resulting peak pattern coincided with the pattern shown in FIG. 5. It was therefore confirmed that the crystal was a crystal of GSSG dilithium salt trihydrate.

Example 4

(1) Acquisition of GSSG Diammonium Salt Trihydrate—1

In water, 25 g of a crystal of GSSG hexahydrate prepared in accordance with the method of Patent Document 2 was dissolved, and then pH was adjusted to 6.2 using ammonia aqueous solution. The solution was diluted with water to prepare 250 mL of an aqueous solution containing 30 g/L of GSSG. The aqueous solution was filtrated with a 0.45 µm filter, and then freeze-dried for 72 hours to obtain a whitish transparent powder. In powder X-ray diffraction measurement of the powder, no X-ray diffraction peak was identified, so that the powder was found to be a non-crystalline amorphous material. From the results of HPLC analysis of the powder, the powder was found to be GSSG diammonium salt. From the above, the powder was found to be a non-crystalline amorphous GSSG diammonium salt.

The non-crystalline amorphous GSSG diammonium salt acquired was spread on a petri dish and left standing still for 2 days to be exposed to an environment with a relative humidity of 75% at 40° C., so that a crystal precipitated.

(2) Acquisition of GSSG Diammonium Salt Trihydrate—2

In water, 120 g of a crystal of GSSG hexahydrate prepared in accordance with the method of Patent Document 2 was dissolved, and the pH was adjusted to 6.2 using 25% ammonia aqueous solution, so that 333 mL of a solution was obtained. To the aqueous solution, 400 mL of methanol was added over a time of 1 hour, and 0.1 g of the crystal acquired in Example 4 (1) described above was added as a seed crystal to precipitate a crystal. The crystal slurry was then cooled to 30° C., and stirred for 24 hours to mature the crystal, which was then filtrated and dried at 30° C. under reduced pressure to obtain 20 g of the crystal.

As a result of powder X-ray diffraction of the resulting crystal, the powder X-ray diffraction pattern of the crystal was as shown in FIG. 7. As a result of powder X-ray diffraction, the diffraction angles of peaks having a relative intensity ratio ($I/I_0$) of 10 or more are shown in Table 7. In the table, "2θ" represents diffraction angle 2θ(°) and "relative intensity" represents relative intensity ratio ($I/I_0$).

TABLE 7

| 2θ | Relative intensity |
|---|---|
| 4.8 | 23 |
| 5.2 | 24 |
| 5.7 | 40 |
| 8.3 | 26 |
| 9.2 | 15 |
| 9.7 | 20 |
| 9.9 | 21 |
| 10.5 | 50 |
| 11.4 | 18 |
| 12.6 | 19 |
| 13.0 | 12 |
| 13.6 | 17 |
| 14.5 | 25 |
| 14.7 | 46 |
| 15.2 | 34 |
| 15.8 | 100 |
| 16.7 | 38 |
| 17.1 | 35 |
| 18.5 | 48 |
| 18.7 | 18 |
| 19.5 | 35 |
| 19.7 | 13 |
| 20.2 | 18 |

TABLE 7-continued

| 2θ | Relative intensity |
|---|---|
| 20.4 | 12 |
| 20.9 | 50 |
| 21.6 | 15 |
| 21.8 | 26 |
| 22.2 | 46 |
| 22.7 | 19 |
| 23.0 | 22 |
| 23.8 | 31 |
| 24.3 | 51 |
| 24.6 | 55 |
| 24.8 | 17 |
| 25.1 | 22 |
| 25.2 | 22 |
| 25.5 | 17 |
| 25.3 | 23 |
| 26.4 | 16 |
| 26.8 | 8 |
| 27.8 | 18 |
| 28.0 | 12 |
| 28.8 | 9 |
| 29.5 | 10 |
| 29.7 | 9 |
| 29.9 | 9 |
| 30.3 | 9 |
| 30.9 | 14 |
| 32.0 | 14 |
| 33.5 | 9 |
| 33.7 | 8 |
| 34.8 | 10 |
| 35.8 | 6 |
| 36.5 | 9 |
| 37.3 | 14 |
| 38.6 | 7 |
| 39.5 | 7 |

The IR analysis result of the resulting crystal was as shown in FIG. 8.

As the HPLC analysis result, the crystal was found to be a crystal of GSSG. The ammonium content of the crystal measured in the HPLC analysis was 5.5 wt % (in terms of anhydrate), which approximately coincided with the theoretical value of diammonium salt (5.3 wt %). The water content in the crystal was 7.3 wt %, which approximately coincided with the theoretical value of trihydrate (7.7 wt %).

From the above, the crystal was found to be a crystal of GSSG diammonium salt trihydrate.

The various physical properties of the crystal are shown in Table 8. The pH of an aqueous solution of 25 g/L of GSSG diammonium salt trihydrate was measured. Measurement of melting point was performed by using Melting Point M-565 (manufactured by BUeCHI) under conditions at 50° C. to 200° C., 0.5° C./min, in accordance with the attached instruction manual.

TABLE 8

| Water content (wt %) | 8.7 |
|---|---|
| ammonium content (wt %) | 5.5 |
| Melting point (° C.) | 184.2 |
| pH | 5.4 |

The crystal acquired in Example 4 (1) used as a seed crystal was also subjected to powder X-ray diffraction measurement, and the resulting peak pattern coincided with the pattern shown in FIG. 7. It was therefore confirmed that the crystal was a crystal of GSSG diammonium salt trihydrate.

Example 5

Solubility of Crystal of GSSG Dication Salt

Each of the crystal of GSSG monohydrate and the crystal of GSSG hexahydrate was added to water adjusted at 25° C. until an excess remained undissolved, and stirred for a sufficient time. The supernatant liquid containing no crystal was then collected, filtered with a 0.45 μm filter. The concentration of GSSG in the solution was measured to calculate the solubility in 100 mL of water.

The solubility of each of the crystals of GSSG dication salts obtained in Examples 1 to 4 was calculated by measuring the weight of each of the dissolved GSSG dication salts when a specified amount of each of the crystals of GSSG dication salts was completely dissolved in a specified amount of water adjusted at 25° C., and converting the measured value to the solubility in 100 mL of water. The value calculated by the method was regarded as the lower limit of the solubility.

The results are shown in Table 9.

TABLE 9

| Sample name | Solubility in 100 mL of water g |
|---|---|
| Crystal of GSSG hexahydrate | 23.3 |
| Crystal of GSSG monohydrate | 1.4 |
| Crystal of GSSG disodium salt hexahydrate | 125.9 or more |
| Crystal of GSSG dipotassium salt trihydrate | 108.6 or more |
| Crystal of GSSG dilithium salt trihydrate | 112.8 or more |
| Crystal of GSSG diammonium salt trihydrate | 119.6 or more |

As shown in Table 9, the crystal of GSSG disodium salt hexahydrate, the crystal of GSSG dipotassium salt trihydrate, the crystal of GSSG dilithium salt trihydrate, and the crystal of GSSG diammonium salt trihydrate had greatly improved solubility in water in comparison with crystals of existing free bodies (crystal of GSSG hexahydrate and crystal of GSSG monohydrate).

Example 6

Storage Stability of Crystal of GSSG Dication Salt

The storage stability of the crystal of GSSG disodium salt hexahydrate and the non-crystalline amorphous GSSG disodium salt which were acquired in Example 1, the crystal of GSSG dipotassium salt trihydrate and the non-crystalline amorphous GSSG dipotassium salt which were acquired in Example 2, the crystal of GSSG dilithium salt trihydrate and the non-crystalline amorphous GSSG dilithium salt which were acquired in Example 3, and the crystal of GSSG diammonium salt trihydrate and the non-crystalline amorphous GSSG diammonium salt which were acquired in Example 4 were compared under conditions at 40° C. and a relative humidity of 75%, based on the percentage of weight increase.

The results are shown in Tables 10 to 13. The percentage of weight increase was calculated taking 100 as the weight of each sample at an elapsed time of 0 hours.

TABLE 10

| Elapsed time | Hours | 0 | 3 | 5 | 24 | 72 |
|---|---|---|---|---|---|---|
| Crystal of disodium salt hexahydrate | % | 0 | 0.4 | 0.7 | 3.1 | 5.8 |
| Non-crystalline amorphous | % | 0 | 0.7 | 1.3 | 5.8 | 10.9 |

TABLE 10-continued

| Elapsed time | Hours | 0 | 3 | 5 | 24 | 72 |
|---|---|---|---|---|---|---|
| material | | | | | | |

TABLE 11

| Elapsed time | Hours | 0 | 3 | 5 | 24 | 72 |
|---|---|---|---|---|---|---|
| Crystal of dipotassium salt trihydrate | % | 0 | 0.2 | 0.3 | 2.3 | 7.9 |
| Non-crystalline amorphous material | % | 0 | 0.6 | 1.0 | 4.7 | 10.0 |

TABLE 12

| Elapsed time | Hours | 0 | 3 | 5 | 24 | 72 |
|---|---|---|---|---|---|---|
| Crystal of dilithium salt trihydrate | % | 0 | 0.4 | 0.7 | 2.6 | 7.3 |
| Non-crystalline amorphous material | % | 0 | 0.7 | 1.3 | 4.6 | 9.7 |

TABLE 13

| Elapsed time | Hours | 0 | 3 | 5 | 24 | 72 |
|---|---|---|---|---|---|---|
| Crystal of diammonium salt trihydrate | % | 0 | 0.2 | 0.3 | 0.5 | 0.2 |
| Non-crystalline amorphous material | % | 0 | 0.7 | 1.1 | 4.8 | 6.8 |

As a result, the crystal of GSSG disodium salt hexahydrate, the crystal of GSSG potassium salt trihydrate, the crystal of GSSG dilithium salt trihydrate, and the crystal of GSSG diammonium salt trihydrate had smaller percentage of weight increase in comparison with the respective non-crystalline amorphous materials. Accordingly, each of the crystals was found to have excellent storage stability with lower hygroscopicity in comparison with non-crystalline amorphous materials.

INDUSTRIAL APPLICABILITY

According to the present invention, a crystal of GSSG dication salt useful, for example, as products, raw materials or intermediates of health foods, pharmaceuticals, or cosmetics, and a method of producing the same are provided.

The invention claimed is:
1. A crystal of oxidized glutathione (hereinafter referred to as GSSG) dication salt, wherein the crystal is
   (a) a crystal of GSSG disodium salt hexahydrate having peaks at diffraction angles 2θ(°) of
      (i) 18.5±0.2°, 20.7±0.2°, 21.3±0.2°, 23.2±0.2° and 23.6±0.2°,
      (ii) 18.5±0.2°, 20.7±0.2°, 21.3±0.2°, 23.2±0.2°, 23.6±0.2°, 18.9±0.2°, 6.4±0.2°, 22.5±0.2°, 12.7±0.2° and 19.4±0.2°, or
      (iii) 18.5±0.2°, 20.7±0.2°, 21.3±0.2°, 23.2±0.2°, 23.6±0.2°, 18.9±0.2°, 6.4±0.2°, 22.5±0.2°, 12.7±0.2°, 19.4±0.2°, 22.0±0.2°, 19.9±0.2°, 22.8±0.2°, 25.6±0.2° and 24.4±0.2°
   in powder X-ray diffraction,
   (b) a crystal of GSSG dipotassium salt trihydrate having peaks at diffraction angles 2θ(°) of
      (i) 23.8±0.2°, 22.1±0.2°, 21.6±0.2°, 25.0±0.2° and 20.4±0.2°,
      (ii) 23.8±0.2°, 22.1±0.2°, 21.6±0.2°, 25.0±0.2°, 20.4±0.2°, 17.5±0.2°, 25.6±0.2°, 26.7±0.2°, 23.3±0.2° and 18.1±0.2°, or
      (iii) 23.8±0.2°, 22.1±0.2°, 21.6±0.2°, 25.0±0.2°, 20.4±0.2°, 17.5±0.2°, 25.6±0.2°, 26.7±0.2°, 23.3±0.2°, 18.1±0.2°, 28.5±0.2°, 27.8±0.2°, 19.2±0.2°, 19.7±0.2° and 31.5±0.2°
   in powder X-ray diffraction,
   (c) a crystal of GSSG dilithium salt trihydrate having peaks at diffraction angles 2θ(°) of
      (i) 18.9±0.2°, 19.3±0.2°, 20.1±0.2°, 20.5±0.2° and 23.5±0.2°,
      (ii) 18.9±0.2°, 19.3±0.2°, 20.1±0.2°, 20.5±0.2°, 23.5±0.2°, 24.6±0.2°, 21.3±0.2°, 20.3±0.2°, 25.9±0.2° and 20.9±0.2°, or
      (iii) 18.9±0.2°, 19.3±0.2°, 20.1±0.2°, 20.5±0.2°, 23.5±0.2°, 24.6±0.2°, 21.3±0.2°, 20.3±0.2°, 25.9±0.2°, 20.9±0.2°, 24.0±0.2°, 4.6±0.2°, 26.2±0.2°, 26.5±0.2° and 22.2±0.2°
   in powder X-ray diffraction, or
   (d) a crystal of GSSG diammonium salt trihydrate having peaks at diffraction angles 2θ(°) of
      (i) 15.8±0.2°, 24.6±0.2°, 24.3±0.2°, 10.5±0.2° and 20.9±0.2°,
      (ii) 15.8±0.2°, 24.6±0.2°, 24.3±0.2°, 10.5±0.2°, 20.9±0.2°, 18.5±0.2°, 14.7±0.2°, 22.2±0.2°, 5.7±0.2° and 16.7±0.2°, or
      (iii) 15.8±0.2°, 24.6±0.2°, 24.3±0.2°, 10.5±0.2°, 20.9±0.2°, 18.5±0.2°, 14.7±0.2°, 22.2±0.2°, 5.7±0.2°, 16.7±0.2°, 19.5±0.2°, 17.1±0.2°, 15.2±0.2°, 23.8±0.2° and 8.3±0.2°
   in powder X-ray diffraction.

2. The crystal according to claim 1, the crystal being a crystal of GSSG disodium salt hexahydrate.

3. The crystal according to claim 2, the crystal having peaks at diffraction angles 2θ(°) of
18.5±0.2°, 20.7±0.2°, 21.3±0.2°, 23.2±0.2°, 23.6±0.2°, 18.9±0.2°, 6.4±0.2°, 22.5±0.2°, 12.7±0.2°, 19.4±0.2°, 22.0±0.2°, 19.9±0.2°, 22.8±0.2°, 25.6±0.2° and 24.4±0.2° in powder X-ray diffraction.

4. The crystal according to claim 1, the crystal being a crystal of GSSG dipotassium salt trihydrate.

5. The crystal according to claim 4, the crystal having peaks at diffraction angles 2θ(°) of
23.8±0.2°, 22.1±0.2°, 21.6±0.2°, 25.0±0.2°, 20.4±0.2°, 17.5±0.2°, 25.6±0.2°, 26.7±0.2°, 23.3±0.2°, 18.1±0.2°, 28.5±0.2°, 27.8±0.2°, 19.2±0.2°, 19.7±0.2° and 31.5±0.2° in powder X-ray diffraction.

6. The crystal according to claim 1, the crystal being a crystal of GSSG dilithium salt trihydrate.

7. The crystal according to claim 6, the crystal having peaks at diffraction angles 2θ(°) of
18.9±0.2°, 19.3±0.2°, 20.1±0.2°, 20.5±0.2°, 23.5±0.2°, 24.6±0.2°, 21.3±0.2°, 20.3±0.2°, 25.9±0.2°, 20.9±0.2°, 24.0±0.2°, 4.6±0.2°, 26.2±0.2°, 26.5±0.2° and 22.2±0.2° in powder X-ray diffraction.

8. The crystal according to claim 1, the crystal being a crystal of GSSG diammonium salt trihydrate.

9. The crystal according to claim 8, the crystal having peaks at diffraction angles 2θ(°) of
15.8±0.2°, 24.6±0.2°, 24.3±0.2°, 10.5±0.2°, 20.9±0.2°, 18.5±0.2°, 14.7±0.2°, 22.2±0.2°, 5.7±0.2°, 16.7±0.2°, 19.5±0.2°, 17.1±0.2°, 15.2±0.2°, 23.8±0.2° and 8.3±0.2° in powder X-ray diffraction.

\* \* \* \* \*